United States Patent
Ly

(10) Patent No.: US 8,541,419 B2
(45) Date of Patent: Sep. 24, 2013

(54) ISOTOPICALLY ENRICHED PYRIMIDIN-5-YL ACETIC ACID DERIVATIVES AS CRTH2 ANTAGONISTS

(75) Inventor: Tai Wei Ly, San Diego, CA (US)

(73) Assignee: Actimis Pharmaceuticals, Inc., San Diego, CA (US)

( * ) Notice: Subject to any disclaimer, the term of this patent is extended or adjusted under 35 U.S.C. 154(b) by 56 days.

(21) Appl. No.: 13/061,921

(22) PCT Filed: Sep. 1, 2009

(86) PCT No.: PCT/US2009/004934
§ 371 (c)(1),
(2), (4) Date: Apr. 5, 2011

(87) PCT Pub. No.: WO2010/027448
PCT Pub. Date: Mar. 11, 2010

(65) Prior Publication Data
US 2011/0172250 A1    Jul. 14, 2011

Related U.S. Application Data

(60) Provisional application No. 61/190,870, filed on Sep. 2, 2008.

(51) Int. Cl.
A01N 43/54 (2006.01)
C07D 239/42 (2006.01)
C07D 239/02 (2006.01)
C07D 401/04 (2006.01)

(52) U.S. Cl.
USPC .......................... 514/256; 544/329

(58) Field of Classification Search
None
See application file for complete search history.

(56) References Cited

U.S. PATENT DOCUMENTS
2011/0034482 A1* 2/2011 Ly ................................ 514/256

FOREIGN PATENT DOCUMENTS
| WO | WO 2004/048343 | 6/2004 |
| WO | WO 2004/096777 | 11/2004 |
| WO | WO 2005/073234 | 8/2005 |

OTHER PUBLICATIONS
Kushner, et. al., Canadian Journal of Physiology and Pharmacology, (1999) 77,2, pp. 79-88.*
Sequin, et. al., Science, (1974); vol. 186, No. 4159, pp. 101-107.*
http://en.wikipedia.org/wiki/Deuterium; last opened on Sep. 19, 2012.*
http://en.wikipedia.org/wiki/Carbon-13; last opened on Sep. 20, 2012.*
Foster, :Deuterium Isotope Effects in the Metabolism of Drugs and Xenobiotics: Implications for Drug Design, Advances in Drug Research, Academic Press, London, GB, 14:1-40 (1985).

* cited by examiner

*Primary Examiner* — Jeffrey Murray
(74) *Attorney, Agent, or Firm* — Jones Day

(57) ABSTRACT

Provided herein are $^2$H- and $^{13}$C-enriched compounds of formula (I) or (II); wherein R is as defined herein, and wherein at least one hydrogen atom, in certain embodiments, three or more hydrogen atoms, are deuterium atoms or at least one carbon atom is a carbon-13 atom. Also provided are pharmaceutical compositions and methods using the $^2$H- and $^{13}$C-enriched compounds, useful for treating CRTH2-related diseases or disorders such as, for example, asthma, allergic rhinitis, atopic dermatitis, allergic conjuvatitis, Churg-Strauss syndrome, sinusitis, basophilic leukemia, chronic urticaria or basophilic leukocytosis.

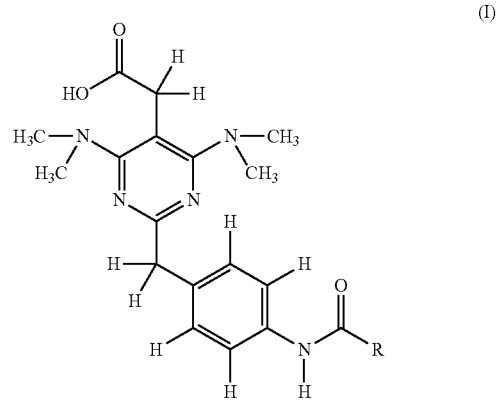

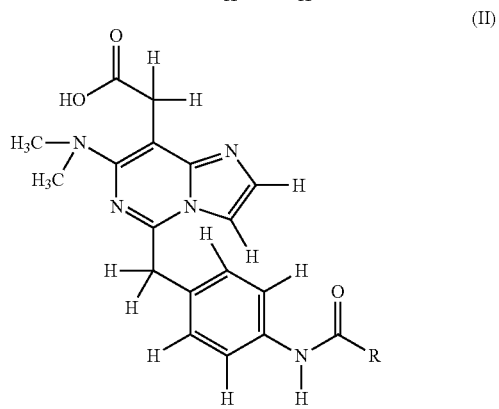

12 Claims, No Drawings

US 8,541,419 B2

1

ISOTOPICALLY ENRICHED PYRIMIDIN-5-YL ACETIC ACID DERIVATIVES AS CRTH2 ANTAGONISTS

CLAIM OF PRIORITY

This application is a 371 of International Patent Application No. PCT/US2009/004934, filed on Sep. 1, 2009, which claims priority to U.S. Provisional Application No. 61/190,870, entitled "Isotopically Enriched Pyrimidin-5-yl Acetic Acid Derivatives as CRTH2 Antagonists," filed Sep. 2, 2008. The disclosure of each of the above-referenced applications is incorporated by reference herein in its entirety.

TECHNICAL FIELD

Provided herein are $^2$H- and $^{13}$C-enriched pyrimidin-5-yl acetic acid derivatives having CRTH2 (G-protein-coupled chemoattractant receptor, expressed on Th2 cells) antagonistic activity, useful for treatment of diseases or disorders such as, for example, asthma, allergic rhinitis, atopic dermatitis, allergic conjuvatitis, Churg-Strauss syndrome, sinusitis, basophilic leukemia, chronic urticaria or basophilic leukocytosis.

BACKGROUND

CRTH2 is G-protein coupled receptor expressed on Th2 cells, eosinophils and basophils that mediates the effects of prostaglandin $D_2$ ($PGD_2$). CRTH2 is a therapeutic target for certain diseases including allergic diseases, such as asthma, exercise induced asthma, allergic rhinitis, atopic dermatitis, allergic conjunctivitis, as well as Churg-Strauss syndrome, sinusitis, basophilic leukemia, chronic urticaria and basophilic leukocytosis. Pyrimidin-5-yl acetic acid derivatives including those described in international patent application publications WO 2004/096777 (published Nov. 11, 2004) or in WO 2005/073234 (published Aug. 11, 2005) are effective antagonists of CRTH2 and promising candidates for use in the treatment of CRTH2-related diseases or disorders. Improvements including without limitation extending pharmacological effective lives and/or decreasing metabolic liabilities in vivo, of therapeutic pyrimidin-5-yl acetic acid derivatives are sought.

SUMMARY

In one aspect, provided herein are isotopically enriched compounds of formula I or II:

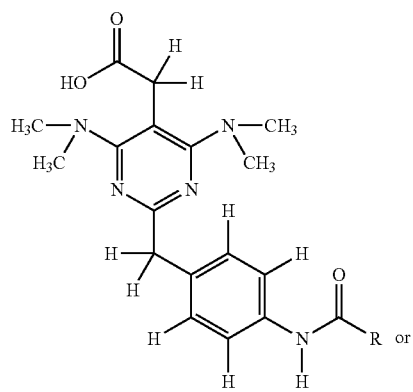

I

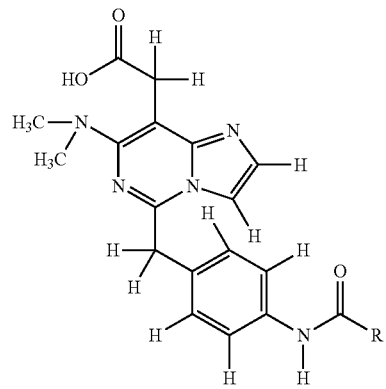

II or pharmaceutically acceptable salts thereof, wherein R is hydrogen, $C_{1-6}$alkyl, $C_{3-8}$ cycloalkyl optionally substituted by $C_{1-6}$ alkyl, or phenyl optionally substituted with 1-4 substituents selected from halogen, $C_{1-4}$ alkyl optionally substituted with mono-, di- or tri-halogen, and $C_{1-4}$ alkoxy; and wherein one or more hydrogen atoms are replaced by a deuterium atom or one or more carbon atoms are replaced by a carbon-13 atom.

In some embodiments, the compounds provided are of formula III or IV:

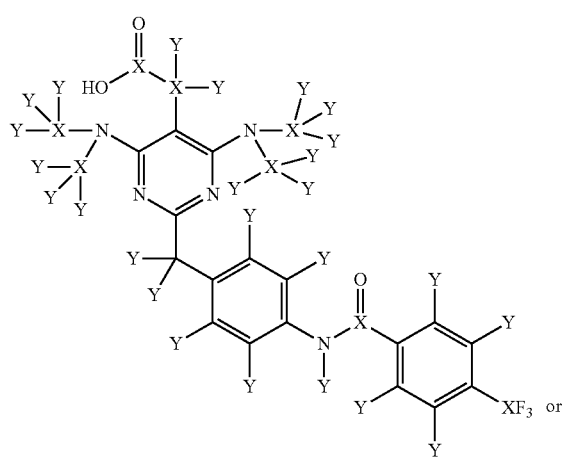

III

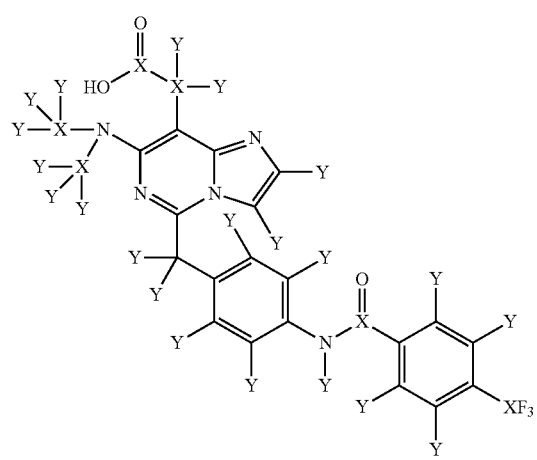

IV wherein each Y atom is a hydrogen atom or deuterium atom; and each X atom is a carbon-12 atom or carbon-13 atom, and wherein at least one Y atom is deuterium or at least one X atom is a carbon-13 atom. In certain embodiments, at least one, two, three, four, five, six or more, or all Y atoms are deuterium. In other embodiments at least one, two, three, four, five, six, seven or all X atoms are carbon-13 atoms.

In some embodiments, the compounds provided herein are of formula V or VI:

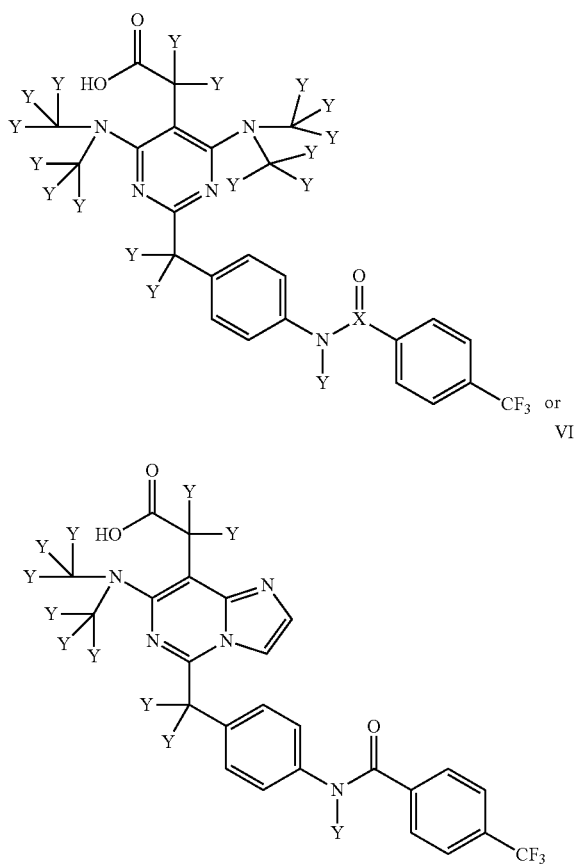

V

VI wherein each Y atom is a hydrogen or a deuterium and at least one Y atom is a deuterium.

In certain embodiments, provided herein are amine salts comprising an $^2$H- and/or $^{13}$C-isotopically enriched acid compound according to any one of formulas I-VI and a pharmaceutically acceptable amine.

In some embodiments the amine salt is crystalline.

In another aspect, provided herein are pharmaceutical compositions comprising a compound of the present disclosure and a pharmaceutically acceptable excipient.

In yet another aspect, provided herein are methods of treating a CRTH2-related disease or disorder in a subject in need thereof. Such methods comprise administering an effective amount of a compound of the present disclosure to a subject in need thereof. In some embodiments, the CRTH2-related disease or disorder is asthma, allergic rhinitis, atopic dermatitis, allergic conjuvatitis, Churg-Strauss syndrome, sinusitis, basophilic leukemia, chronic urticaria or basophilic leukocytosis.

In one aspect, provided herein are compounds of the present disclosure for use in the preparation of a medicament for treating a CRTH2-related disease or disorder. In some embodiments, the CRTH2-related disease or disorder is asthma, allergic rhinitis, atopic dermatitis, allergic conjuvatitis, Churg-Strauss syndrome, sinusitis, basophilic leukemia, chronic urticaria or basophilic leukocytosis.

In one aspect, provided herein are methods of modulating activity of CRTH2 comprising administering a compound of the present disclosure to a subject in need thereof in an amount effective to antagonize CRTH2 activity.

In another aspect, provided herein is an $^2$H- and/or $^{13}$C-enriched isotopologue of a compound as described in WO 2004/096777 (published Nov. 11, 2004) or in WO 2005/073234 (published Aug. 11, 2005), the contents of which are each hereby incorporated by reference in its entirety for all purposes, wherein at least one hydrogen atom is replaced by a deuterium atom, at least one carbon atom is replaced by a carbon-13 atom, or at least one hydrogen atom is replaced by a deuterium atom and at least one carbon atom is replaced by a carbon-13 atom.

In another aspect, provided herein is an $^2$H- and/or $^{13}$C-enriched isotopologue of an amine salt compound as described in U.S. Provisional Application No. 60/936,736, filed Jun. 21, 2007, the contents of which is hereby incorporated by reference in its entirety for all purposes, wherein at least one hydrogen atom is replaced by a deuterium atom, at least one carbon atom is replaced by a carbon-13 atom, or at least one hydrogen atom is replaced by a deuterium atom and at least one carbon atom is replaced by a carbon-13 atom. Pharmaceutical compositions and methods of using such $^2$H- and/or $^{13}$C-enriched isotopologues are provided herein.

DETAILED DESCRIPTION

Terminology

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

As used herein, alkyl per se and "alk" and "alkyl" used in combinations such as alkoxy or alkylamino represent a linear or branched alkyl radical having, if not otherwise specified, one to six carbon atoms. The number of carbon atoms is specified in an alkyl group by terms such as, for example, "$C_{1-4}$ alkyl," which in this example represents an alkyl radical having one to four carbon atoms. Exemplary alkyl groups include, for instance, methyl, ethyl, n-propyl, isopropyl, tert-butyl, n-pentyl and n-hexyl.

"Alkoxy" as used herein represents —OR where R is alkyl as defined above. Exemplary alkoxy groups include, for instance, methoxy, ethoxy, n-propoxy, isopropoxy, n-pentoxy and n-hexoxy.

"Cycloalkyl" as used herein represents a saturated cyclic alkyl group having, if not otherwise specified, three to eight carbon atoms. Exemplary cycloalkyl groups include, for instance, cyclopropyl, cyclobutyl, cyclopentyl, cyclohexyl and cycloheptyl.

"Alkyl," "alkoxy," and "cycloalkyl" groups recited herein are optionally substituted with one or more deuterium atoms, wherein the deuterium composition of the atom or atoms is other than the natural isotopic composition.

The carbon atoms of the "alkyl," "alkoxy," and "cycloalkyl" groups recited herein optionally comprise carbon-13 at an amount greater than the natural isotopic composition for carbon atoms.

As used herein, "halo", "halogen" or "halide" refers to F, Cl, Br or I.

Unless otherwise stated, when a position is designated as "H" or "hydrogen," or when a position in a chemical structure provided herein is implicitly occupied by a hydrogen atom, the position will be understood to have hydrogen at its natural isotopic composition.

Unless otherwise stated, when a position is designated as "C" or "carbon," or when a position in a chemical structure provided herein is understood to those skilled in the art to be a carbon atom, the position will be understood to have carbon at its natural isotopic composition.

Both "$^2$H" and "D" refer to deuterium.

As used herein, "isotopic composition" refers to the amount of each isotope present for a given atom. By "natural isotopic composition" it is meant the naturally occurring isotopic composition for a given atom. Unless otherwise designated, the atoms of the compounds recited herein represent a stable isotope of those atoms.

It will be recognized that some variation of natural isotopic abundance occurs in a synthesized compound depending upon the origin of chemical materials used in the synthesis. Thus, typically, any preparation of a compound will inherently contain small amounts of deuterated and/or $^{13}$C-containing isotopologues. The concentration of naturally abundant stable hydrogen and carbon isotopes, notwithstanding this variation, is small and immaterial as compared to the degree of stable isotopic substitution of compounds as provided herein.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom. For example, in a compound as provided herein, when a position is designated as having deuterium, it will be understood that the abundance of deuterium at that position is substantially greater than the natural abundance of deuterium, which is about 0.015%. In a compound as provided herein, when a position is designated as having carbon-13 (also termed $^{13}$C), it will be understood that the abundance of carbon-13 at that position is substantially greater than the natural abundance of carbon-13, which is about 1.109%. Hence, "isotopic enrichment" can be expressed in terms of the percentage of incorporation of an amount of a specific isotope at a given atom in a molecule in the place of the atom's natural isotopic abundance. For example, deuterium enrichment of 1% at a given position means that 1% of molecules in a given sample contain deuterium at the specified position.

The term "isotopic enrichment factor" as used herein means the ratio between the isotopic abundance and the natural abundance of a specific isotope.

A compound as provided herein designated as having deuterium typically has a minimum isotopic enrichment factor of at least 3000 (a deuterium enrichment of 45%) at each atom designated in the compound. In other embodiments, a compound as provided herein has an isotopic enrichment factor for each designated deuterium atom of at least 3500 (52.5% deuterium enrichment), at least 4000 (60% deuterium enrichment), at least 4500 (67.5% deuterium enrichment), at least 5000 (75% deuterium enrichment), at least 5500 (82.5% deuterium enrichment), at least 6000 (90% deuterium enrichment), at least 6333.3 (95% deuterium enrichment), at least 6466.7 (97% deuterium enrichment), at least 6600 (99% deuterium enrichment), or at least 6633.3 (99.5% deuterium enrichment).

A compound as provided herein designated as having carbon-13 typically has a minimum isotopic enrichment factor of at least 40 (44.4% $^{13}$C enrichment) at each atom designated in the compound. In other embodiments, a compound as provided herein has an isotopic enrichment factor for each designated carbon-13 atom of at least 45 (50% $^{13}$C enrichment), at least 54.1 (60% $^{13}$C enrichment), at least 60.9 (67.5% $^{13}$C enrichment), at least 67.6 (75% $^{13}$C enrichment), at least 74.4 (82.5% $^{13}$C enrichment), at least 81.1 (90% $^{13}$C enrichment), at least 85.7 (95% $^{13}$C enrichment), at least 87.5 (97% $^{13}$C enrichment), at least 89.3 (99% $^{13}$C enrichment), or at least 89.7 (99.5% $^{13}$C enrichment).

The isotopic enrichment of the compounds provided herein can be determined using conventional analytical methods known to one of ordinary skill in the art, including mass spectrometry and nuclear magnetic resonance spectroscopy.

The term "isotopologue" as used herein refers to a species of a specific compound that differs from another species of the given compound only in its isotopic composition.

The term "compound" as used herein is intended to include any salts or solvates, including hydrates, thereof.

The term "pharmaceutically acceptable" as used herein refers to a component that is compatible with other ingredients of a pharmaceutical composition and is suitable for use in contact with the tissues of a subject without undue toxicity, irritation, allergic response, immunogenecity or other complications, commensurate with a reasonable benefit/risk ratio.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces. The term "hydrate" is employed when the solvent is water. Pharmaceutically acceptable solvates and hydrates are complexes of a compound with one or more solvent or water molecules, or 1 to about 100, or 1 to about 10, or one to about 2, 3 or 4, solvent or water molecules.

A salt of a compound provided herein is formed between an acid and a basic group of the compound, such as, for instance, an amino functional group, or between a base and an acidic group of the compound, such as, for instance, a carboxyl functional group.

Salts of a compound provided herein include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Suitable acid salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see *Handbook of Pharmaceutical Salts: Properties, Selection, and Use*, Stahl and Wermuth (eds.), Verlag Helvetica Chimica Acta/Wiley-VCH, Zurich 2002.

"Subject" as used herein refers to an animal, including a mammal such as, for instance, a dog, cat, mouse, rat, rabbit or human.

As used herein, the term "treat," "treating" and "treatment" refer to amelioration or beneficially altering one or more symptoms of a disease or disorder.

The term "therapeutically effective amount" refers to the amount of a compound that, when administered, is sufficient to ameliorate or otherwise beneficially alter one or more of the symptoms of a disease or disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

As used herein, "$IC_{50}$" refers to an amount, concentration or dosage of a particular test compound that achieves a 50% inhibition of a maximal response, such as modulation of CRTH2 activity, in an assay that measures such response.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC), infrared spectroscopy (IR), gas chromatography (GC), ultraviolet spectroscopy (UV), nuclear magnetic resonance (NMR) and mass spectrometry (MS), used by those of skill in the art to assess such purity, or sufficiently pure such that further purification would not detectably alter the physical and chemical properties, such as enzymatic and biological activities, of the substance. In certain embodiments, "substantially pure" refers to a collection of molecules, wherein at least about 50%, at least about 70%, at least about 80%, at least about 90%, at least about 95%, at least about 98%, at least about 99%, or at least about 99.5% of the molecules are a single compound or are a single isotopologue, including a racemic mixture or single stereoisomer thereof, as determined by standard analytical methods. Methods for purification of the compounds to produce substantially chemically pure compounds are known to those of skill in the art. A substantially chemically pure compound may, however, be a mixture of stereoisomers. In such instances, further purification might increase the specific activity of the compound.

Embodiments

Provided herein are compounds, compositions and methods useful in the modulation of CRTH2 activity. The compounds provided herein are isotopically enriched for deuterium or carbon-13, which inhibit at least one function of a mammalian CRTH2 protein, and which have utility for the treatment of diseases or disorders such as, for example, asthma, allergic rhinitis, atopic dermatitis, allergic conjuvatitis, Churg-Strauss syndrome, sinusitis, basophilic leukemia, chronic urticaria or basophilic leukocytosis. The ability of the compounds provided herein to inhibit a function of a CRTH2 protein can be demonstrated in binding assays (e.g., ligand binding or agonist binding), signaling assays (e.g., activation of a G-protein or calcium mobilization), cellular response assays (e.g., eosinophil migration or CD4+ T cell migration) and/or physiological response assays (e.g., contact hypersensitivity animal model). Exemplary assays, as well as representative activities in such assays of non-isotopically enriched isotopologues of exemplary compounds and amine salts thereof provided herein, are described in international patent application publications WO 2004/096777 and WO 2005/073234, and in U.S. Provisional Application No. 60/936,736, filed Jun. 21, 2007, the contents of which are each hereby incorporated by reference in their entireties for all purposes.

Without intent to be limited by any theory or mechanism, it is believed that the greater atomic masses of deuterium or carbon-13 relative to hydrogen or carbon in the compounds provided herein can reduce the rates that such compounds are metabolized without impairing the desired pharmacological effects of such compounds with results that lower doses or fewer doses in a course of dose administration of such compounds to a subject are required.

Compounds

In one aspect, provided herein is a isotopically enriched compound of formula I or II:

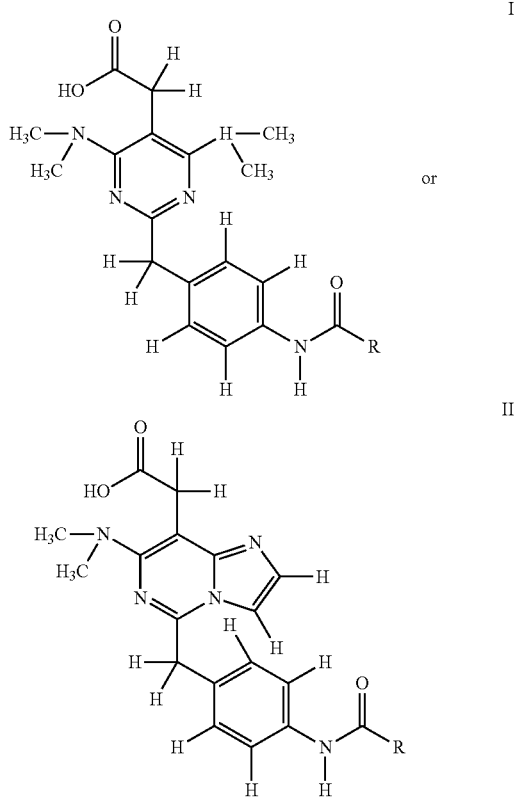

where R is defined below and where one or more hydrogen atoms in formula I or II are replaced by a deuterium atom or one or more carbon atoms in formula I or II are replaced by a carbon-13 atom. In certain embodiments, the compound is isotopically enriched for deuterium. In other embodiments, the compound is isotopically enriched for carbon-13. In yet other embodiments, the compound is isotopically enriched for deuterium and carbon-13.

In formula I and II, R is hydrogen, $C_{1-6}$ alkyl, $C_{3-8}$ cycloalkyl optionally substituted by $C_{1-6}$ alkyl, or phenyl optionally substituted with 1-4 substituents selected from halogen, $C_{1-4}$ alkyl optionally substituted with mono-, di- or tri-halogen, and $C_{1-4}$ alkoxy, wherein any hydrogen is optionally replaced with a deuterium atom or any carbon atom is optionally replaced with a carbon-13 atom. In certain embodiments, R is substituted phenyl.

In certain embodiments, the compound provided is of formula I wherein each hydrogen is replaced by a deuterium atom.

In some embodiments, the compound provided is of formula I wherein 1, 2, 3, 4, 5, 6, 7, 8, 9, 10, 11, 12, 13, 14, 15, 16, 17 or more hydrogens are replaced by deuterium.

In certain embodiments, the compound provided is of formula II wherein each hydrogen is replaced by a deuterium atom.

In some embodiments, the compound provided is of formula II wherein 1, 2, 3, 4, 5, 6, 7, 8, 9, 10, 11 or more hydrogens are replaced by deuterium.

In the above embodiments where hydrogen is replaced with deuterium at a given position, the deuterium isotopic enrichment factor is generally at least 3000 at that position.

In certain embodiments, the compound provided is of formula I wherein 1, 2, 3, 4, 5, 6, 7, 8 or more carbons are replaced by carbon-13.

In certain embodiments, the compound provided is of formula II wherein 1, 2, 3, 4, 5, 6, 7, 8 or more carbons are replaced by carbon-13.

In the above embodiments where carbon is replaced with carbon-13 at a given position, the carbon-13 isotopic enrichment factor is generally at least 40 at that position.

In further embodiments, provided herein is a compound of formula III or IV:

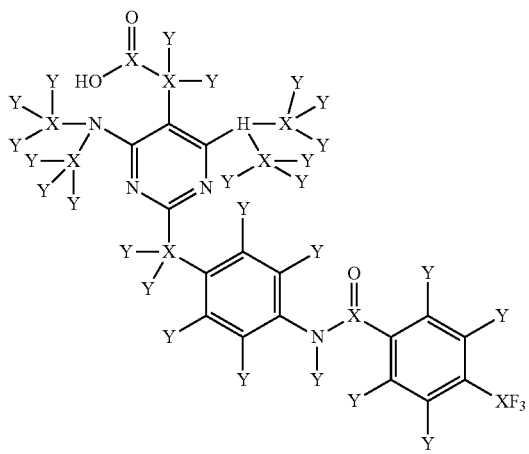

wherein each Y is a hydrogen atom or deuterium atom; each X is a carbon atom or carbon-13 atom, and wherein at least one Y is deuterium or at least one X is a carbon-13 atom. It will be understood that in formula III or IV, any hydrogen or carbon not designated as X or Y is present at its natural isotopic abundance.

In certain embodiments, the compound provided is of formula III wherein each Y is a deuterium atom. In some embodiments at least 1, 2, 3, 4, 5, 6, 7, 8, 9, 10, 11, 12, 13, 14, 15, 16 or 17 Y atoms are deuterium.

In certain embodiments, the compound provided is of formula IV wherein each Y is a deuterium atom. In some embodiments at least 1, 2, 3, 4, 5, 6, 7, 8, 9, 10 or 11 Y atoms are deuterium.

In some embodiments, the compound provided is of formula III wherein each X is carbon-13. In some embodiments 1, 2, 3, 4, 5, 6 or 7 X atoms are carbon-13.

In other embodiments, the compound provided is of formula IV wherein each X is carbon-13. In some embodiments 1, 2, 3, 4, 5 or 6 X atoms are carbon-13.

In certain embodiments of formula III or IV where a given Y atom is deuterium, the deuterium isotopic enrichment factor is of at least 3000 at that position.

In some embodiments of formula III or IV where a given X atom is carbon-13, the carbon-13 isotopic enrichment factor is of at least 40 at that position.

In yet other embodiments, the compound provided herein is of formula V or VI:

wherein each Y atom is a hydrogen or a deuterium and at least one Y atom is a deuterium.

In still other embodiments, the compound provided herein is selected from the group consisting of:
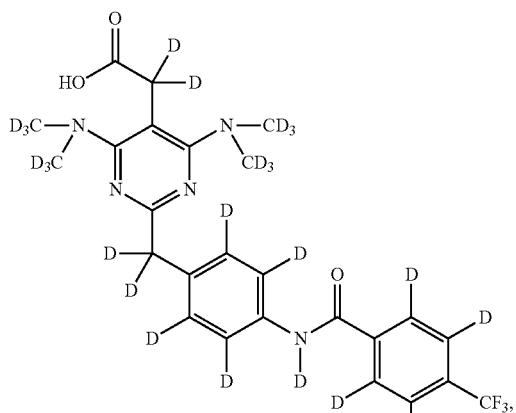
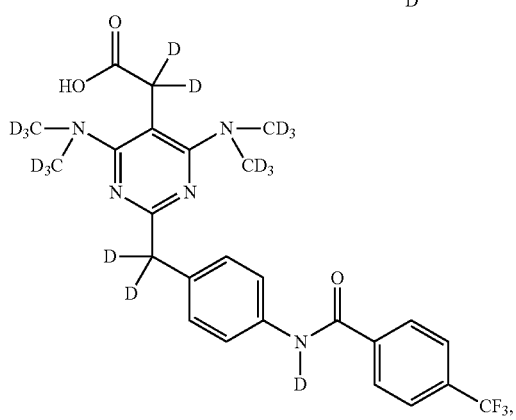
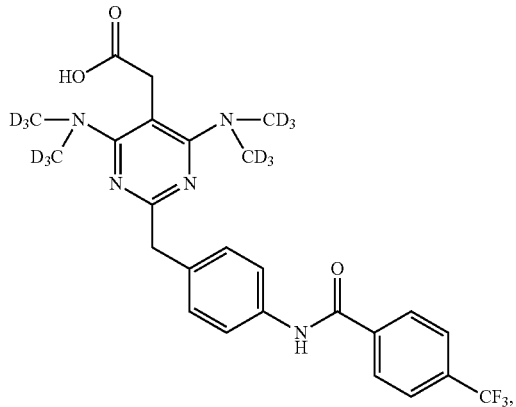
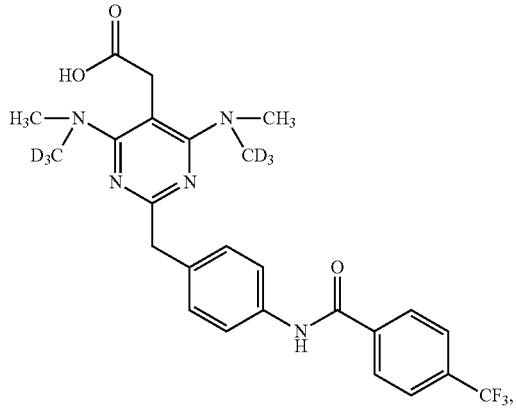
-continued
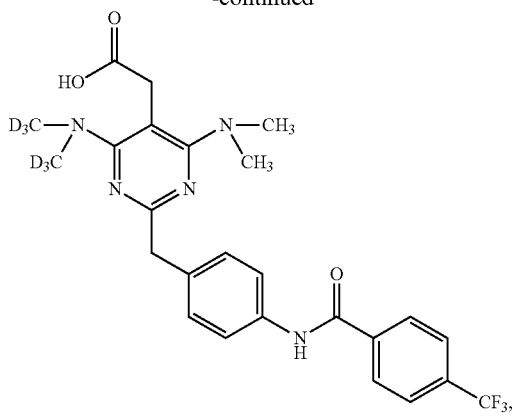
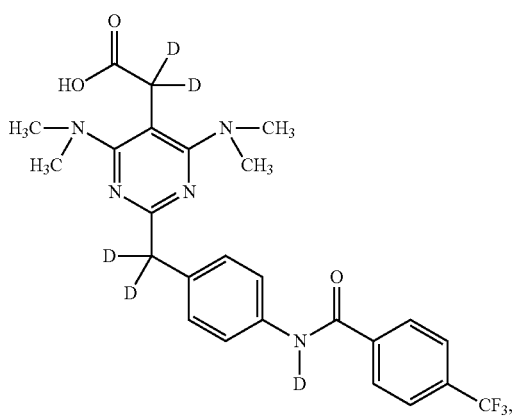
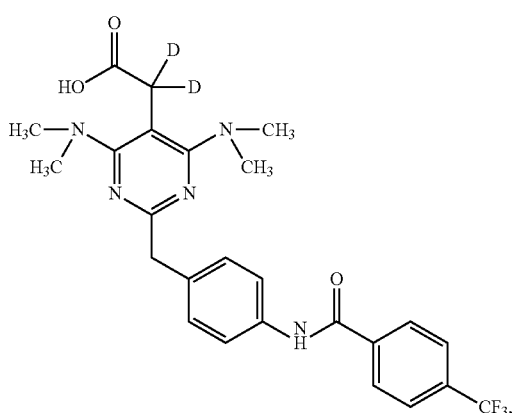
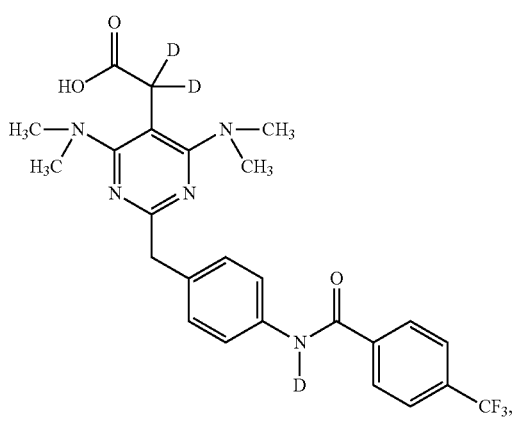

-continued
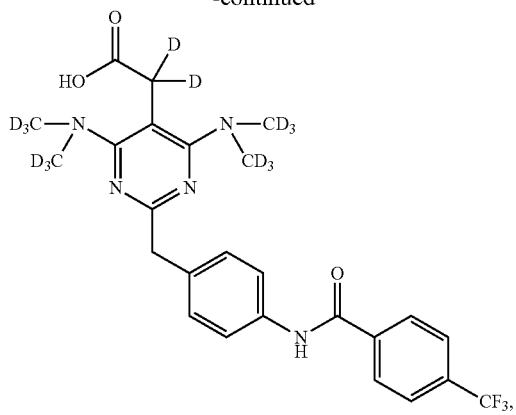
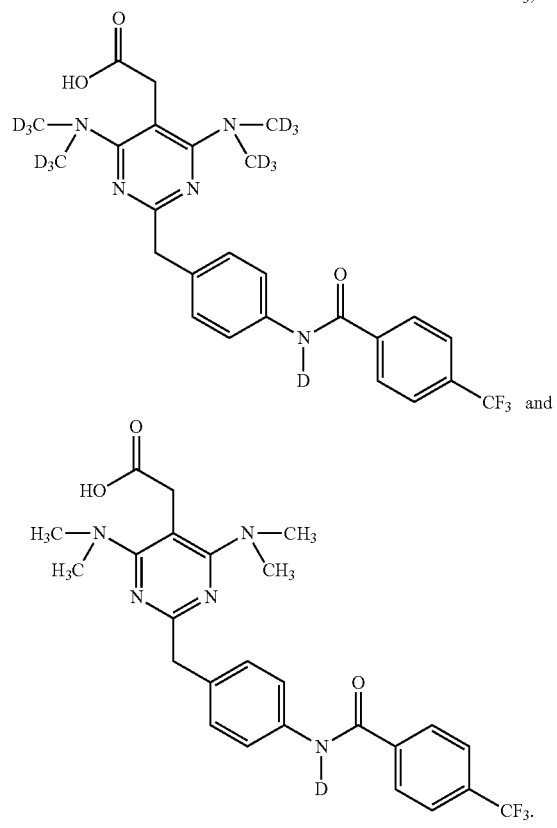
In other embodiments, the compound provided herein is selected from the group consisting of:
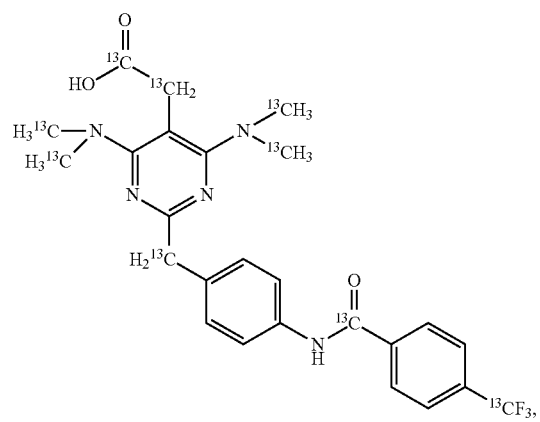
-continued
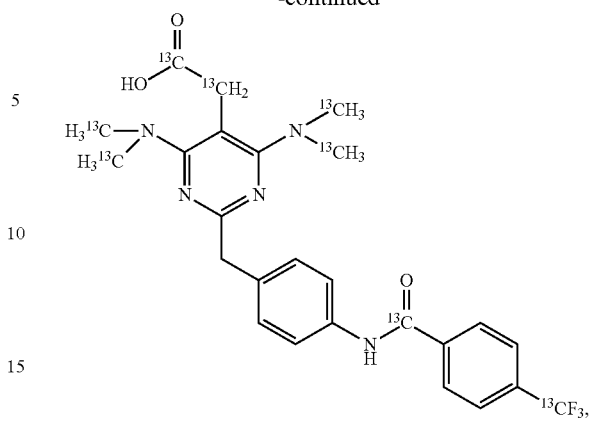
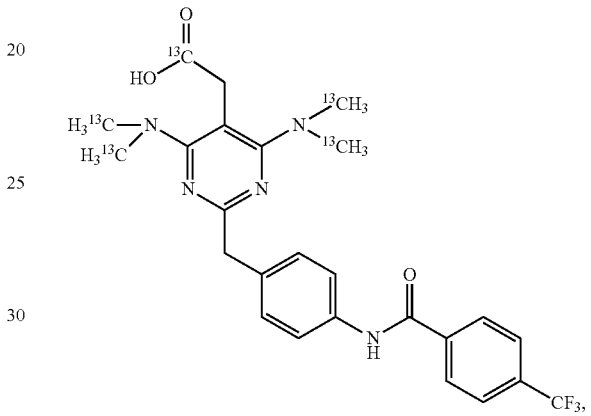
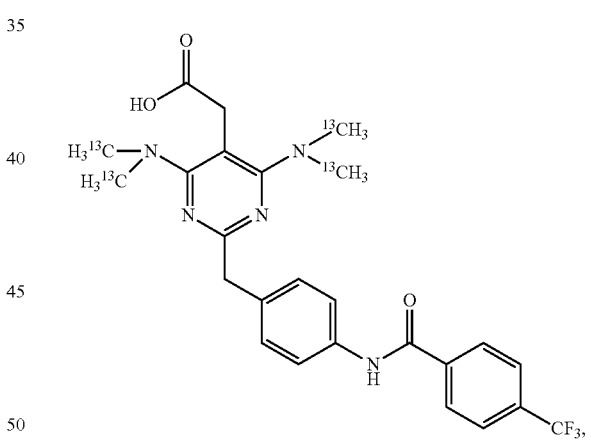
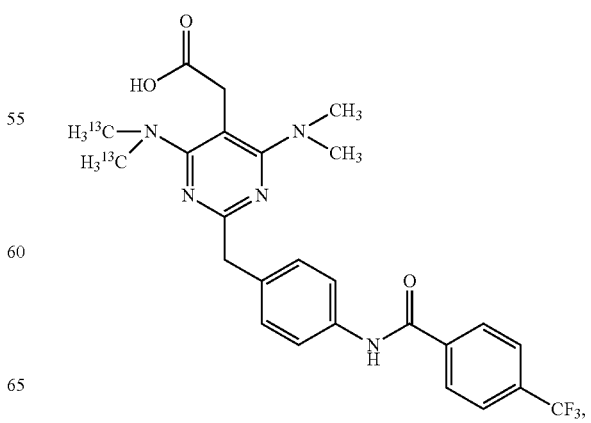

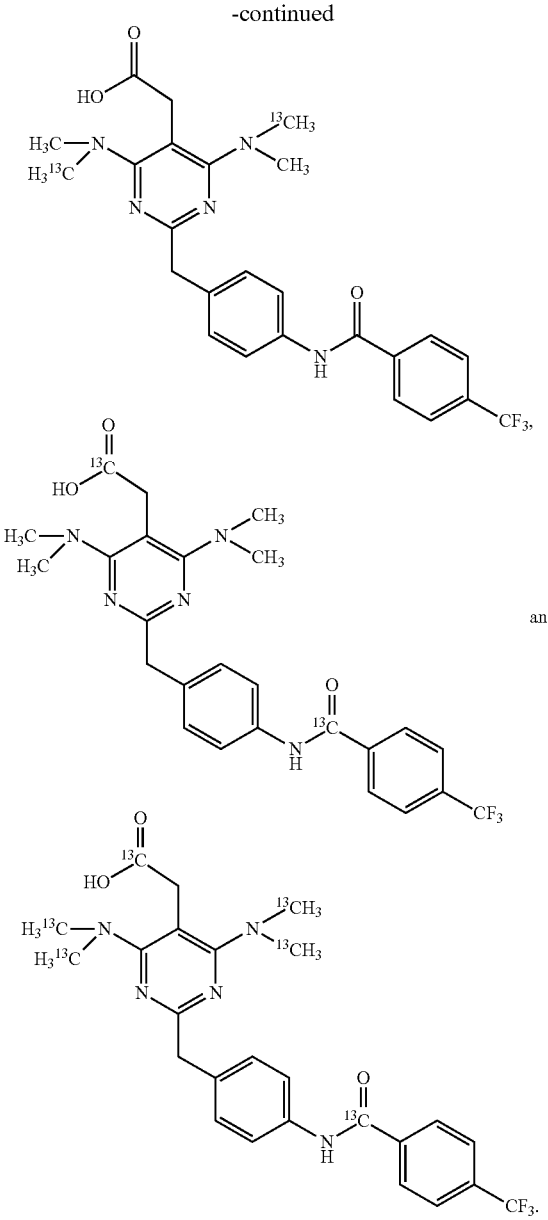
In yet other embodiments, the compound provided herein is selected from the group consisting of:
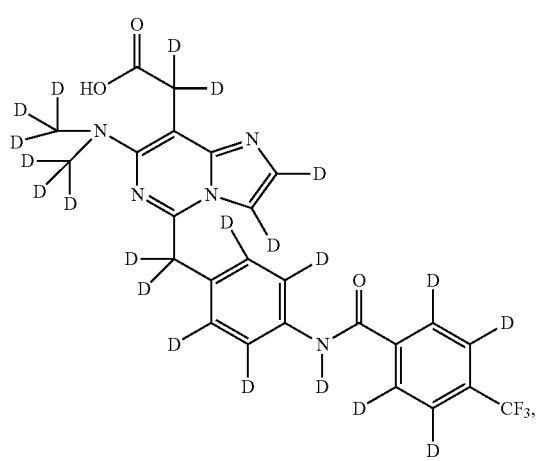
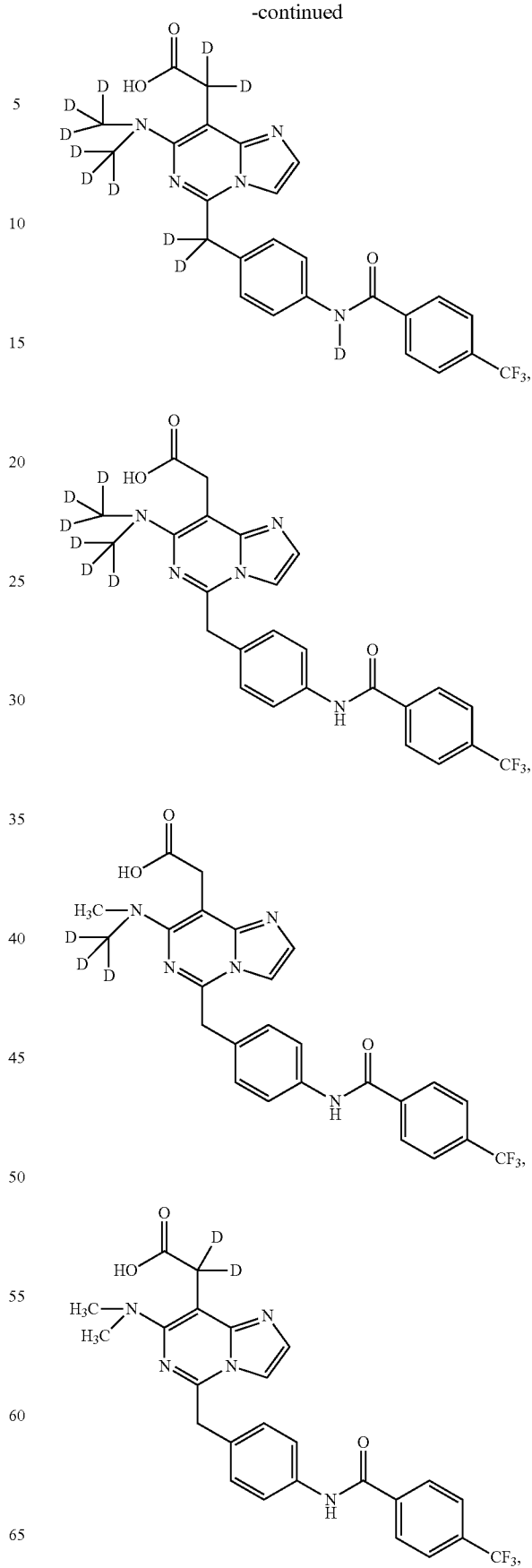
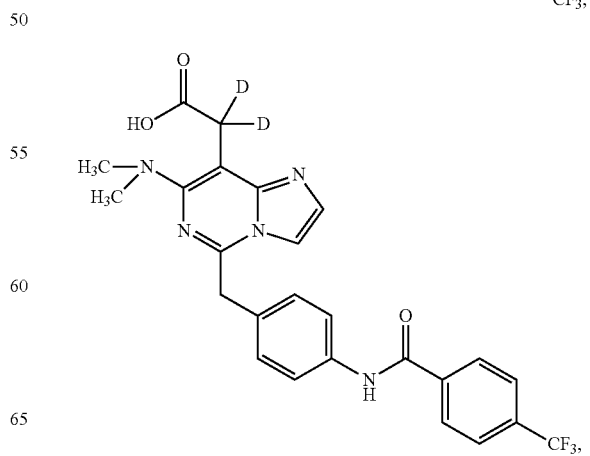

-continued
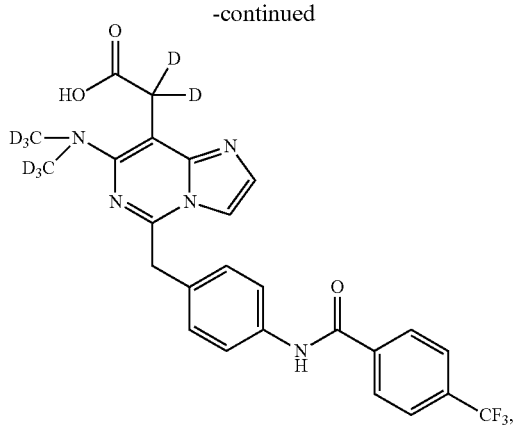
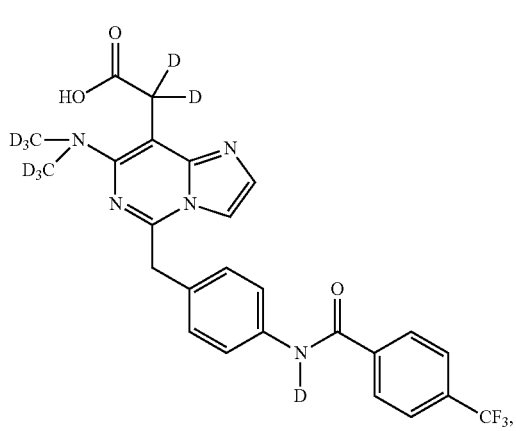
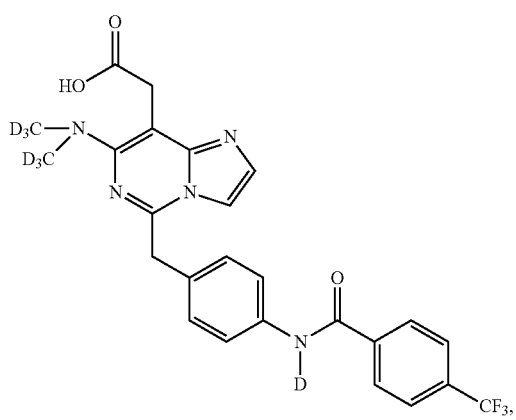
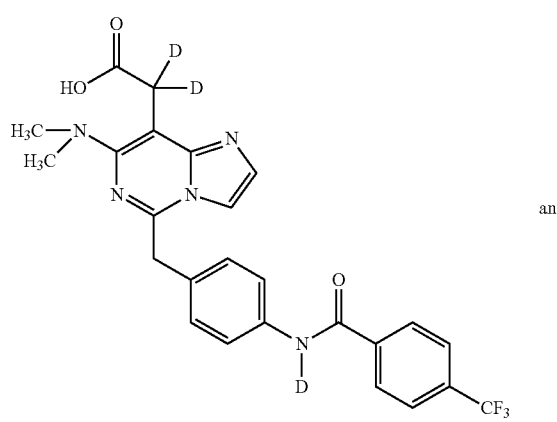
and
-continued
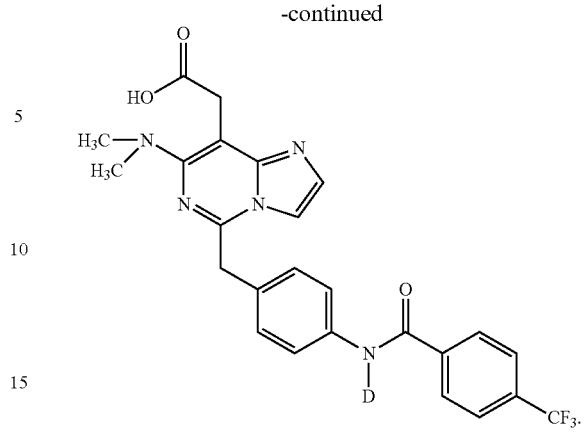
In other embodiments, the compound provided herein is selected from the group consisting of:
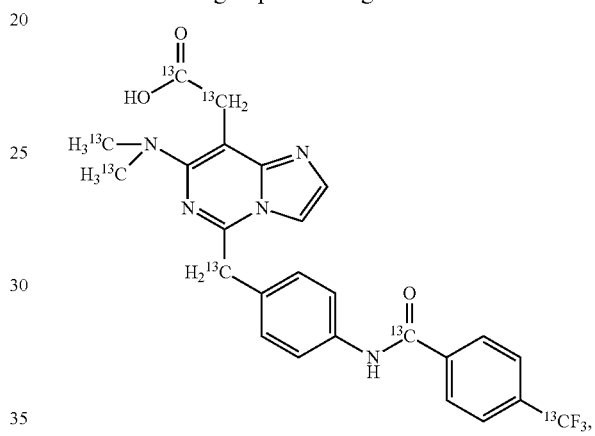
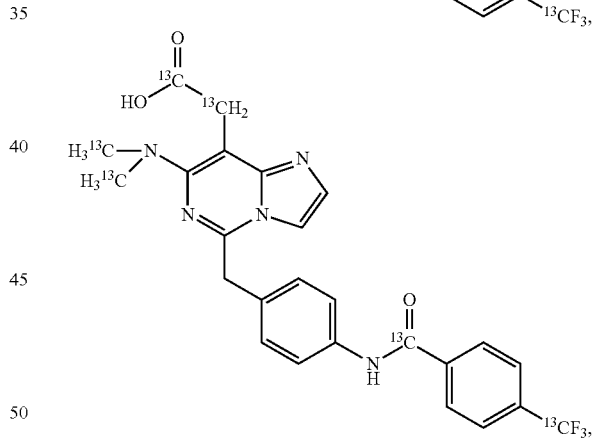
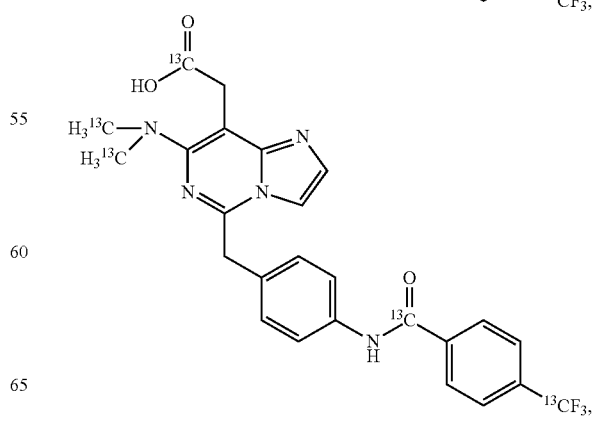

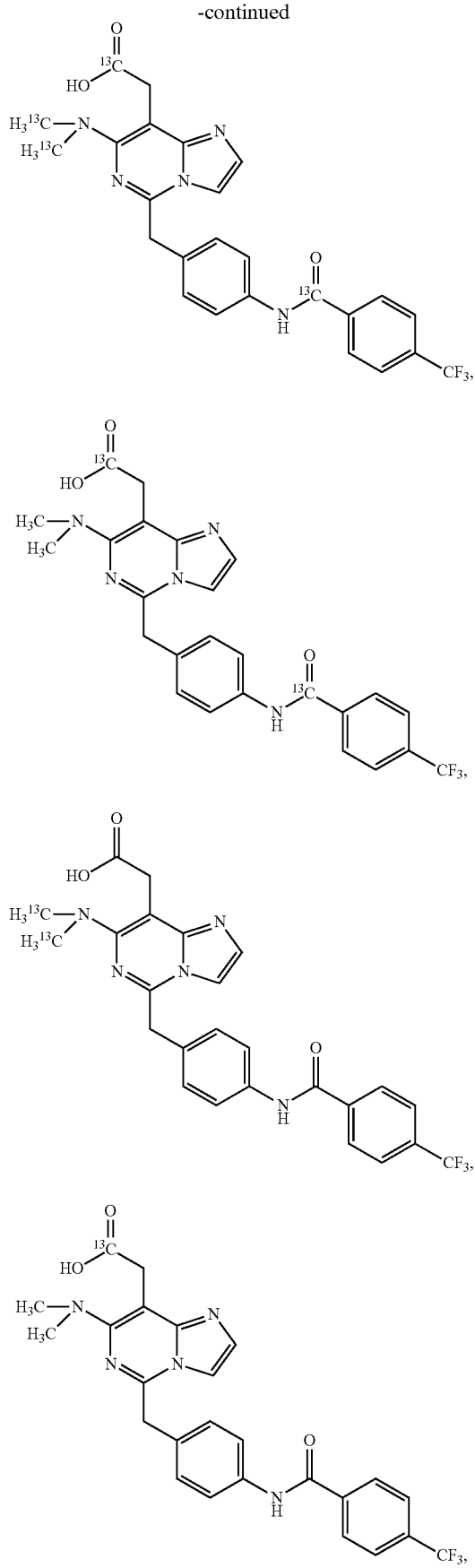
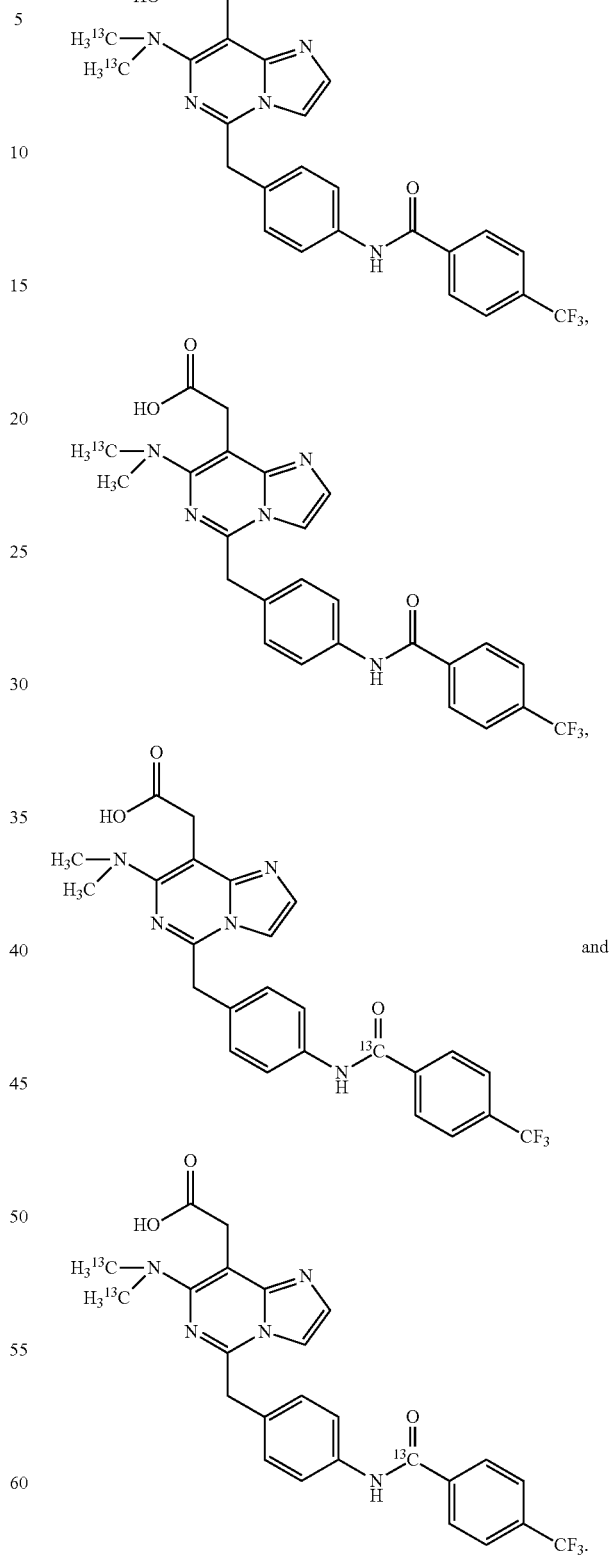
In certain embodiments, provided herein is $^2$H- or $^{13}$C-isotopically enriched {4,6-bis(dimethylamino)-2-(4-(4-(trifluoromethyl)benzamido)benzyl)pyrimidin-5-yl} acetic acid, or an amine salt of $^2$H- or $^{13}$C-isotopically enriched {4,6-bis(dimethylamino)-2-(4-(4-(trifluoromethyl)benzamido)benzyl)pyrimidin-5-yl} acetic acid.

In certain embodiments, provided herein is a pharmaceutically acceptable salt of a compound of any one of formula I-VI.

In certain embodiments, provided herein are amine salts comprising an $^2$H- and/or $^{13}$C-isotopically enriched acid compound according to any one of formulas I-VI and a pharmaceutically acceptable amine. The molar ratio of the acid of any one of formulas I-VI versus the amine is from about 0.5 to about 10, from 0.5 to about 5, from about 0.5 to about 3, from about 0.5 to about 2, or from about 0.8 to about 1.2, or about 1. Suitable amines for use in the amine salts provided herein include, but are not limited to, primary amines, including methylamine, ethylamine, ethanolamine, tris(hydroxymethyl)aminomethane, and ethylenediamine; secondary amines, including dimethylamine, diethylamine, diisopropylamine, dibutylamine, di-sec-butylamine, dicyclohexylamine, diethanolamine, meglumine, pyrrolidine, piperidine, piperazine, and benzathine; tertiary amines, including trimethylamine, triethylamine, triethanolamine, and 1-(2-hydroxyethyl)-pyrrolidine; quaternary ammoniums, including choline, tetra-methylammonium, and tetraethylammonium. For a review on additional amines, see *Handbook of Pharmaceutical Salts: Properties, Selection, and Use* by Stahl and Wermuth (Wiley-VCH, 2002). In some embodiments, the amine in an amine salt is not ethanolamine, triethylamine, and tris(hydroxymethyl)aminomethane.

In another embodiment, the pharmaceutical acceptable amine is a diamine. The pharmaceutically acceptable diamine has first and second amino groups, which each are independently a primary, secondary, or tertiary amino group, or quaternary ammonium group. Suitable diamines for use in the diamine salt include, but are not limited to, ethylenediamine, piperazine, and benzathine. The diamine salt of the acetic acid of any one of formulas I-VI comprises from about 1 to about 3, from about 1.5 to about 2.5, from about 1.75 to about 2.25, or about 2 molar equivalents of the acid of any one of formulas I-VI for one molar equivalent of the diamine. In one group of the diamine salts of this embodiment, the first amino group of the diamine is a primary amino group, and the second amino group is independently a primary, secondary, or tertiary amino group, or quaternary ammonium. In another group of the diamine salts, the first amino group is independently a secondary amino group, and the second amino group is a primary, secondary, or tertiary amino group, or quaternary ammonium. In yet another group of the diamine salts, the first amino group is independently a tertiary amino group, and the second amino group is a primary, secondary, or tertiary amino group, or quaternary ammonium. In yet another group of the diamine salts, the first amino group is a quaternary ammonium, and the second amino group is independently a primary, secondary, or tertiary amino group, or quaternary ammonium.

In yet other embodiments, the amine salt comprises a $^2$H- and/or $^{13}$C-isotopically enriched acid compound according to any one of formulas I-VI and a monoamine. In exemplary groups within these embodiments, the monoamine salt comprises from about 0.5 to about 1.5, from about 0.75 to about 1.25, or about 1 molar equivalent(s) of the acid of a compound according to any one of formulas I-VI for a molar equivalent of the monoamine.

In one group of the monoamine salts of these embodiments, the monoamine of the monoamine salts has a primary amino group. In another group of the monoamine salts, the monoamine has a secondary amino group. In yet another group of the monoamine salts, the monoamine has a tertiary amino group. In still another group of the monoamine salts, the monoamine has a quaternary ammonium group.

In another aspect, provided herein is an $^2$H- and/or $^{13}$C-enriched isotopologue of a compound as described in WO 2004/096777 (published Nov. 11, 2004) or in WO 2005/073234 (published Aug. 11, 2005), the contents of which are each hereby incorporated by reference in its entirety for all purposes, wherein at least one hydrogen atom is replaced by a deuterium atom, at least one carbon atom is replaced by a carbon-13 atom, or at least one hydrogen atom is replaced by a deuterium atom and at least one carbon atom is replaced by a carbon-13 atom.

In another aspect, provided herein is an $^2$H- and/or $^{13}$C-enriched isotopologue of an amine salt compound as described in U.S. Provisional Application No. 60/936,736, filed Jun. 21, 2007, the contents of which is hereby incorporated by reference in its entirety for all purposes, wherein at least one hydrogen atom is replaced by a deuterium atom, at least one carbon atom is replaced by a carbon-13 atom, or at least one hydrogen atom is replaced by a deuterium atom and at least one carbon atom is replaced by a carbon-13 atom.

The compounds provided herein can also be used in the form of prodrugs which include esters. Examples of such esters useful as prodrugs for compounds containing carboxyl groups can be found on pages 14-21 of *Bioreversible Carriers in Drug Design: Theory and Application*, E. B. Roche, Ed. (Pergamon Press, New York, 1987), incorporated herein by reference. Representative carboxy protecting groups are $C_{1-8}$ alkyl (e.g., methyl, ethyl or tert-butyl and the like); haloalkyl; alkenyl; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryl-oxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyl-oxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonyl-aminoalkyl, such as t-butyloxycarbonylaminomethyl and the like; alkylaminocarbonylaminoalkyl, such as methylaminocarbonylaminomethyl and the like; alkanoylaminoalkyl, such as acetyl-aminomethyl and the like; heterocycliccarbonyloxyalkyl, such as 4-methylpiperazinyl-carbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl) alkyl, such as (5-t-butyl-2-oxo-1,3-dioxolen-4-yl)methyl and the like; and (5-phenyl-2-oxo-1,3-dioxolen-4-yl) alkyl, such as (5-phenyl-2-oxo-1,3-dioxolen-4-yl)methyl and the like.

Preparation of Compounds

Compounds as provided herein can be, but are not limited to be, prepared by combining various known methods. Exemplary syntheses are described in the schemes and Examples provided below. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in *Protective Groups in Organic Synthesis* (3rd Edition) by Greene and Wuts (John Wiley and Sons, New York 1999), incorporated herein by reference. For instance, Scheme I below provides a nonlimiting example of a synthesis of an exemplary compound of formula II.

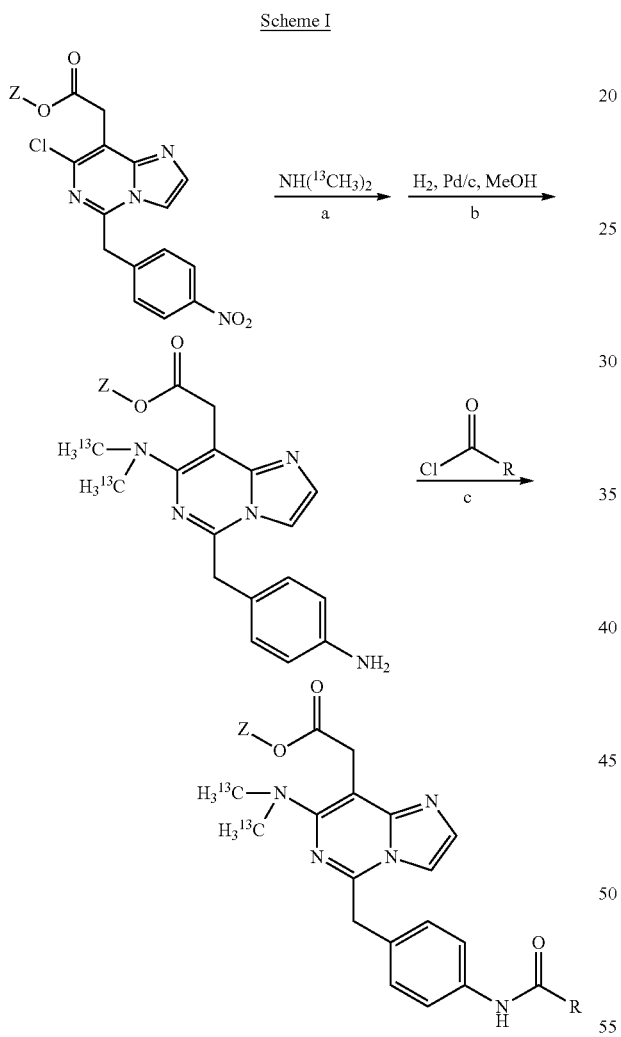

In Scheme I, the starting material, methyl 2-(7-chloro-5-(4-nitrobenzyl)imidazo[1,2-c]pyrimidin-8-yl)acetate, can be prepared, for instance, according to Method I in WO 2005/073234, incorporated herein by reference. R is the same as defined above and Z is a protecting group such as those known to those skilled in the art. The protective group, Z, can be removed to yield a compound with a carboxyl functional group by using a base including, for instance, sodium hydroxide, lithium hydroxide and potassium hydroxide, or an acid including, for instance, HCl, HBr, trifluoroacetic acid and BBr$_3$.

Scheme II provides a nonlimiting example of the synthesis of an exemplary compound of formula II.

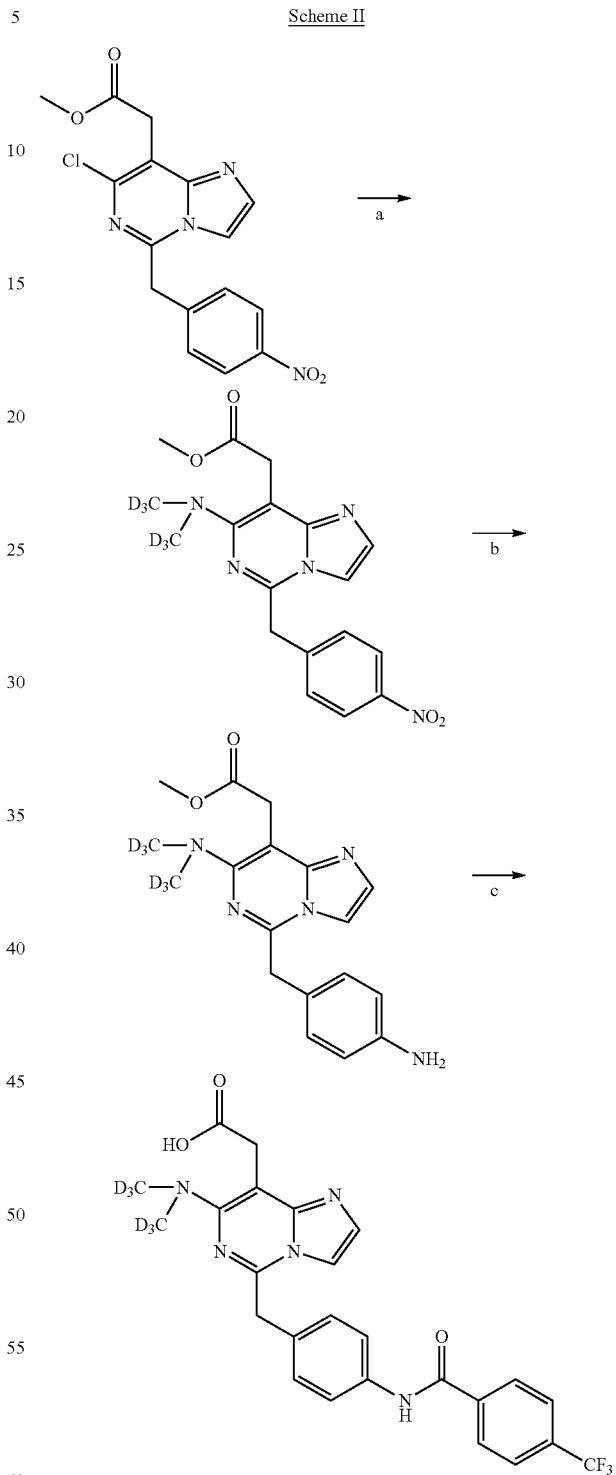

In Scheme II, the starting material, methyl 2-(7-chloro-5-(4-nitrobenzyl)imidazo[1,2-c]pyrimidin-8-yl)acetate, can be prepared, for instance, according to Method I in WO 2005/073234.

Scheme III provides a nonlimiting example of the synthesis of an exemplary compound of formula I.

Scheme III

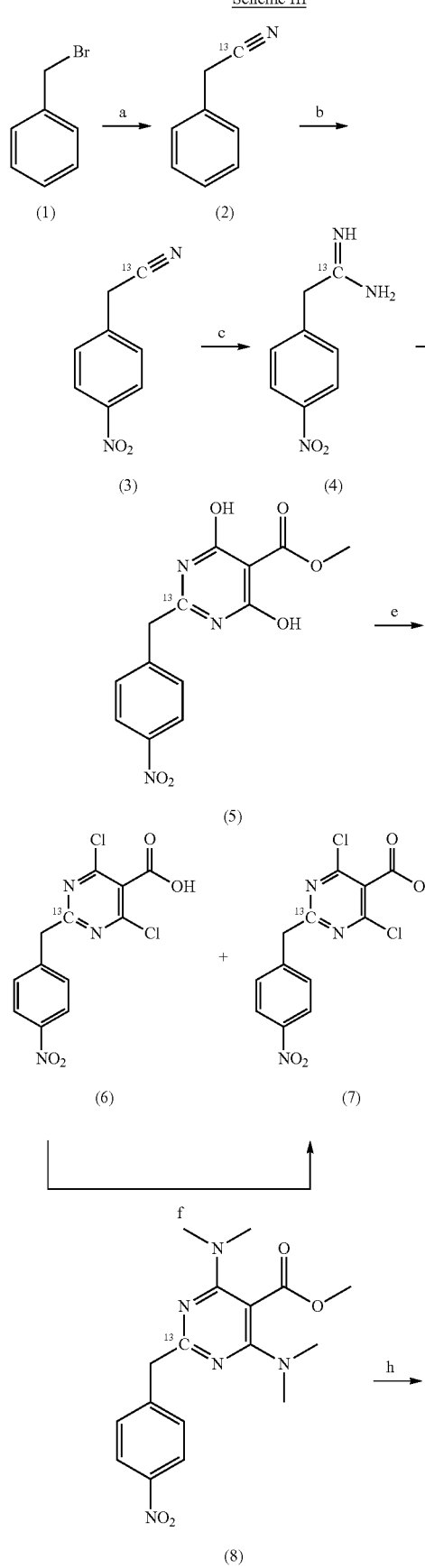
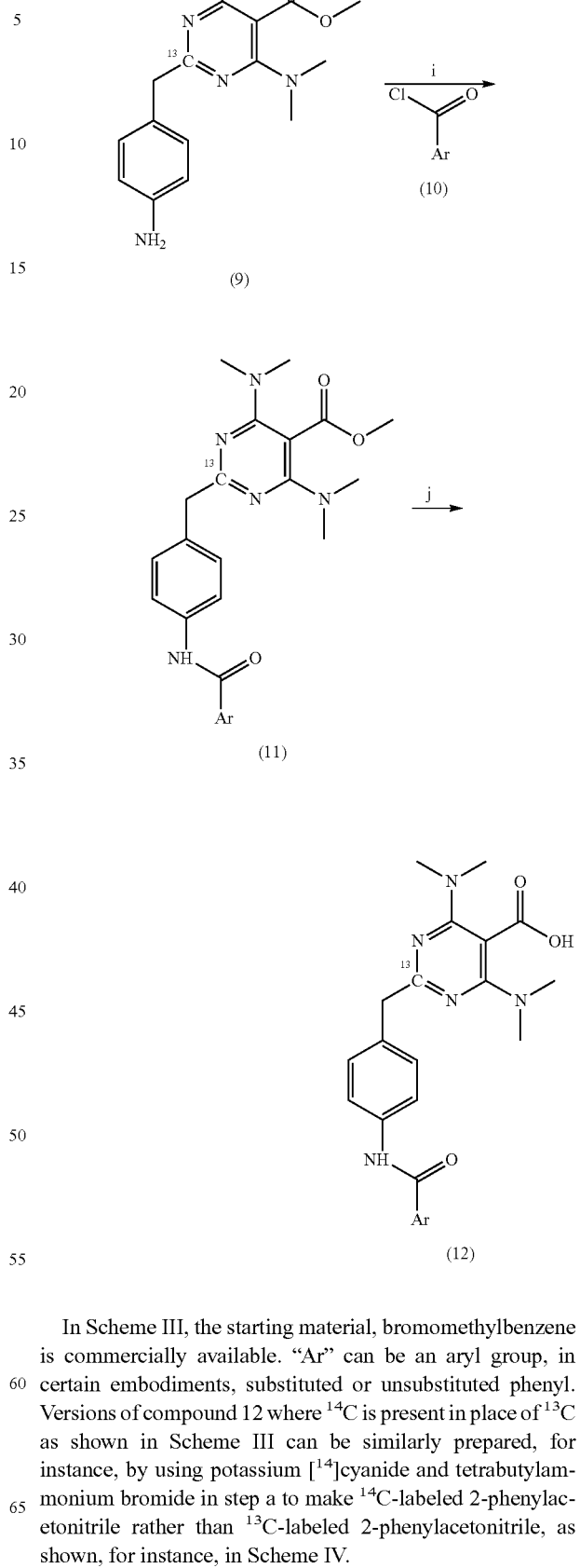

In Scheme III, the starting material, bromomethylbenzene is commercially available. "Ar" can be an aryl group, in certain embodiments, substituted or unsubstituted phenyl. Versions of compound 12 where $^{14}C$ is present in place of $^{13}C$ as shown in Scheme III can be similarly prepared, for instance, by using potassium [$^{14}$]cyanide and tetrabutylammonium bromide in step a to make $^{14}C$-labeled 2-phenylacetonitrile rather than $^{13}C$-labeled 2-phenylacetonitrile, as shown, for instance, in Scheme IV.

Scheme IV
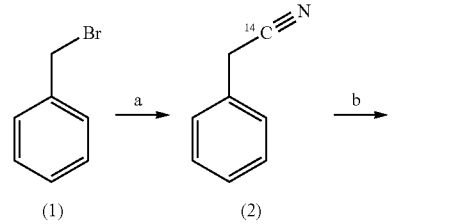
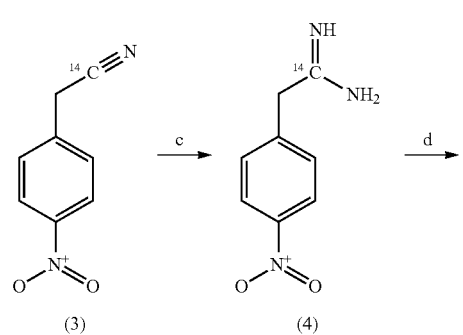
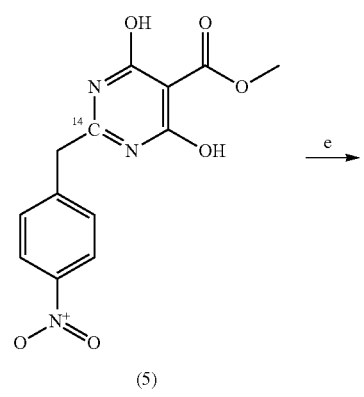
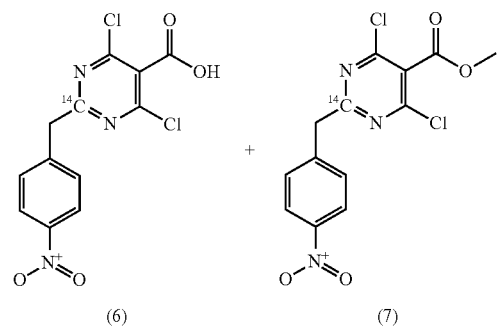
In addition, compounds provided herein can be prepared following the exemplary methods provided in WO 2004/

096777 and WO 2005/073234, the contents of which are each hereby incorporated by reference in its entirety for all purposes, with slight modifications to incorporate $^2$H and/or $^{13}$C isotopically enriched starting materials or reagents or invoking standard synthetic protocols known in the art for introducing isotopic atoms to a chemical structure.

Commercial sources for $^2$H and/or $^{13}$C isotopically enriched starting materials or reagents include, among others, Icon Services Inc. (Summit, New Jersey USA), Cambridge Isotope Laboratories (Andover, Mass. USA) and Sigma-Aldrich Corp. (St. Louis, Mo. USA). Methods of incorporating deuterium and/or carbon-13 in target compounds are extensively documented. See, for instance, *Journal of Labelled Compounds and Radiopharmaceuticals* (John Wiley & Sons Ltd.), for numerous issues that provided detailed experimental descriptions on incorporation of deuterium and/or carbon-13 into bioactive organic molecules.

In another aspect, processes for preparing an amine salt of the acid compound of any one of formulas I-VI are provided herein. Such processes can be performed, for example, according to procedures described and referenced in U.S. Provisional Application No. 60/936,736, filed Jun. 21, 2007, incorporated herein by reference.

Compositions

In one aspect, provided herein is a pharmaceutical composition comprising an active ingredient, that is, a compound of the present disclosure and/or a pharmaceutically acceptable salt, amine salt, solvate or prodrug thereof, and one or more pharmaceutically acceptable excipients. Excipients are inert substances such as, without limitation, carriers, diluents, fillers, coloring agents, flavoring agents, sweeteners, lubricants, solubilizers, suspending agents, binders, vehicles, wetting agents, tablet disintegrating agents and encapsulating material. The choice of excipient, to a large extent, depends on factors, such as the particular mode of administration, the effect of the excipient on the solubility and stability of the active ingredient, and the nature of the dosage form.

Pharmaceutical compositions as provided herein are prepared by combining a therapeutically effective amount of a compound described above together with one or more pharmaceutically acceptable excipients therefore. In making the pharmaceutical compositions, the active ingredient may be mixed with a diluent, or enclosed within a carrier, which may be in the form of a capsule, sachet, paper, or other container. As explained below, the pharmaceutical compositions can be suitable for oral, parenteral or other type of administration to a subject. The pharmaceutical compositions can be in a solid, semi-solid, or liquid form, for example, in the form of tablets, soft or hard gelatin capsules, depots, pills, powders, lozenges, elixirs, suspensions, emulsions, slurrys, solutions, sterile injectable solutions, sterile packaged powders, suppositories, suspensions, syrups, aerosols, ointments, and the like. In certain embodiments, the pharmaceutical compositions contain, for example, up to 0.5%, up to 1%, or up to 10% or more by weight of the active ingredient. Pharmaceutical compositions provided herein may be formulated according to conventional pharmaceutical practice (see, e.g., *Remington: The Science and Practice of Pharmacy*, 21st edition, A. R. Gennaro, ed. (Lippincott Williams & Wilkins, Philadelphia Pa., 2005) and *Encyclopedia of Pharmaceutical Technology, Third Edition*, J. Swarbrick, editor (Informa Healthcare USA, Inc., New York, 2006)).

In powder forms, a carrier may be a finely divided solid which is in admixture with the finely divided active ingredient. The active ingredient may be mixed with a carrier having binding properties in suitable proportions and compacted in the shape and size desired to produce tablets.

The powders and tablets, in certain embodiments, contain from about 1 to about 99 weight percent of the active ingredient. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Pharmaceutical compositions may be presented in unit dose forms containing a predetermined amount of active ingredient per unit dose, suitable for administration to a subject. Such a unit may contain, for example, 0.5 mg to 1200 mg, in some embodiments, 1 mg to 1000 mg, in certain embodiments, 5 mg to 400 mg of a compound as described herein, depending on the condition being treated, the route of administration and the age, weight and condition of the patient. Unit dose forms, as used herein, refer to physically discrete units suitable for administration to human and animal subjects and packaged individually as is known in the art. Each unit dose contains a predetermined quantity of the active ingredient(s) sufficient to produce the desired therapeutic effect, in association with the pharmaceutical excipients. Examples of unit dose forms include ampoules, syringes, and individually packaged tablets and capsules. Unit dose forms may be administered in fractions or multiples thereof.

Methods

A compound of the present disclosure can be administered to a subject for the treatment of a CRTH2-related disease or disorder. In certain aspects, methods are provided comprising administering a compound of the present disclosure to a subject in need thereof in an amount effective for treatment of a CRTH2-related disease or disorder. The compound of the present disclosure can be administered, for example, in as pharmaceutically acceptable salt, amine salt, solvate or prodrug form, pharmaceutical composition or unit dose form as described above.

The disorders and diseases treatable with one or more of compounds provided herein include, but are not limited to, asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the CRTH2-related disease or disorder is asthma, allergic rhinitis, atopic dermatitis, allergic conjuvatitis, Churg-Strauss syndrome, sinusitis, basophilic leukemia, chronic urticaria or basophilic leukocytosis.

The compound provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Advantageously, the $^2$H- and/or $^{13}$C-enriched compounds as provided herein may be suitable for administration in smaller doses, or may be suitable for fewer multiple administrations, to a subject than the corresponding non-$^2$H- and/or $^{13}$C-enriched isotopologues, for example, those described in WO 2004/096777, WO 2005/073234 and U.S. Provisional Application No. 60/936,736, filed Jun. 21, 2007.

In certain embodiments, a compound of the present disclosure is administered to a subject in an oral form, such as, without limitation, a normal or enteric coated tablet, capsule, pill, powder, granule, elixir, tincture, solution, suspension, syrup, solid and liquid aerosol, emulsion and so forth. Oral administration can include, for instance, buccal, lingual or sublingual administration.

In certain embodiments, for oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In other embodiments, the compound is administered in a parenteral form, such as, without limitation, intravenous, intraperitoneal, subcutaneous, intramuscular, and the like forms, well-known to those of ordinary skill in the pharmaceutical arts. The compound provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical sciences.

The compounds of the present disclosure can be administered in intranasal form via topical use of suitable intranasal vehicles, or via transdermal routes, using transdermal delivery systems well-known to those of ordinary skilled in the art.

The dosage regimen with the use of the compounds provided herein is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

Typical dosages of the compound provided herein, when used for the indicated effects, will range from about 0.01 mg/kg/day to about 10 mg/kg/day. In certain embodiments the dosage can range from about 1 mg/kg/day to about 10 mg/kg/day.

The compounds provided herein may be administered in a single daily dose, or the total daily dose may be administered in divided doses, two, three, or more times per day. Where delivery is via transdermal forms, of course, administration is continuous.

In one aspect, provided herein are methods of modulating activity of CRTH2 comprising administering a compound of the present disclosure to a subject in need thereof in an amount effective to antagonize CRTH2 activity.

The $^2$H- and $^{13}$C-enriched compounds provided herein are also useful as analytical reagents for determining the concentration of non-isotopically-enriched compounds in solution.

EXAMPLES

Provided below are examples that by no means should be construed as defining the metes and bounds of any invention described herein.

In the examples below, all quantitative data, if not stated otherwise, related to percentages by weight. Unless otherwise noted, reactions and manipulations were performed at room temperature in an inert gas atmosphere (argon). Unlabeled reagents and solvents were purchased from commercial suppliers and used without further purification. High pressure liquid chromatography (HPLC) spectra were performed and recorded using a HP 1050 SERIES II liquid chromatography system (Hewlett-Packard; Waldbronn, Germany), UV signals were recorded by the work station of the chromatograph. Gas chromatography (GC) spectra were obtained using a HP 5890 gas chromatograph (Hewlett-Packard; Waldbronn, Germany) equipped with EZ-FLASH GC accessory (ThermoScientific; Breda, Netherlands; 10 m RTX-1 capillary, internal diameter 0.25 mm) using helium as carrier gas. Gas chromatograph-mass spectrometry (GC/MS) analyses were obtained using a HP 6890 GC system equipped with a HP 5973 mass spectrometer (Hewlett-Packard; Waldbronn, Germany) having a 25 m fused silica capillary with an internal diameter of 0.2 mm. The stationary phase was cross linked methyl silicone (Hewlett-Packard; Waldbronn, Germany). Helium was used as carrier gas. Mass spectrometric analyses were obtained using a Q-Star-Pulsar mass spectrometer with API source (SCIEX, Toronto, Canada). Nuclear magnetic resonance (NMR) spectra were recorded on a Bruker DRX 400 spectrometer (Bruker; Rheinstetten, Germany). Preparative HPLC was performed using a combined system equipped with a WELLCHROM MAXI-STAR K 1000 pump (Knauer; Berlin, Germany), a KNAUER Variable Wavelength monitor (Knauer; Berlin, Germany) as detector and a MERCK/HITACHI D-2500A Chromato-Integrator (Merck; Darmstadt, Germany) as integrator.

Example 1

[4,6-bis([$^2$H$_6$]dimethylamino)-2-(4-{[4-(trifluoromethyl)benzoyl]amino}benzyl)pyrimidin-5-yl]acetic acid (1)

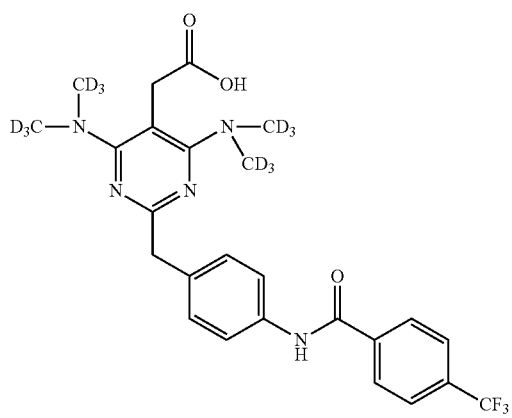

Deuterated [4,6-bis([$^2$H$_6$]dimethylamino)-2-(4-{[4-(trifluoromethyl)benzoyl]amino}benzyl)pyrimidin-5-yl]acetic acid (1) containing twelve deuterium labels in the dimethylamine moieties was synthesized with a purity of >97%, as described below.

Step 1: Synthesis of 2-(4-nitrophenyl)ethanimidamide hydrochloride

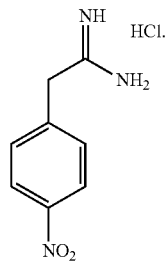 [SMILES: N=C(N)Cc1ccc([N+](=O)[O-])cc1]

A suspension of (4-nitrophenyl)acetonitrile (4.86 g, 30.0 mmol) in ethanol (6 mL, 99 mmol) in a 250 mL round bottom flask was slowly treated at room temperature with 4N hydrochloric acid in dioxane (38 mL, 152 mmol) and stirred for 22 hours. After carefully removing the solvent under water aspirator vacuum at 40° C. the obtained wet pale yellow product was suspended in 21 mL ethanol. Then, a 7N ammonia solution in methanol (12 mL, 84 mmol) was slowly added giving a pale gray suspension. After stirring for two hours additional 2 mL (14 mmol) 7N ammonia solution in methanol were added. After further stirring for one hour at room temperature all volatiles were removed under water aspirator vacuum at 40° C. To remove residues of ethanol and dioxane methyl t-butyl ether (30 mL) was added and once more all volatiles were removed under water aspirator vacuum at 40° C. giving an off-white solid. The crude product was used without purification in the next step.

Step 2: Synthesis of methyl [4,6-dihydroxy-2-(4-nitrobenzyl)-pyrimidin-5-yl]acetate

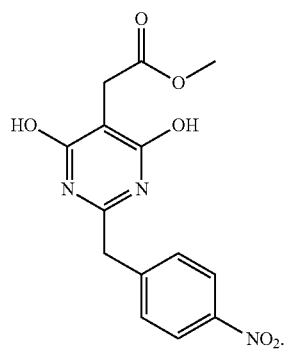 [SMILES: COC(=O)Cc1c(Cl)nc(Cc2ccc([N+](=O)[O-])cc2)nc1Cl]

A 250 mL round bottom flask was charged with 2-(4-nitrophenyl)ethanimidamide hydrochloride (approximately 6.47 g, 30.0 mmol, 48% purity), triethyl ethane-1,1,2-tricarboxylate (7.60 mL, 33.0 mmol) and methanol (43 mL). To this solution was added a 25% sodium methoxide solution in methanol (24.0 mL, 105.2 mmol) immediately resulting in a dark purple thick suspension. After stirring for three hours under reflux the dark purple mixture was cooled to 0° C. using an ice bath and carefully treated with 30 mL water. This mixture was slowly treated with 35 mL 6N hydrochloric acid giving a pale green suspension. The suspension was stirred for additional 30 minutes, filtered and the obtained fawn solid was washed with 100 mL water. The product was dried in a desiccator under vacuum for two days. The crude product was used without purification in the next step.

Step 3: Synthesis of methyl [4,6-dichloro-2-(4-nitrobenzyl)pyrimidin-5-yl]acetate

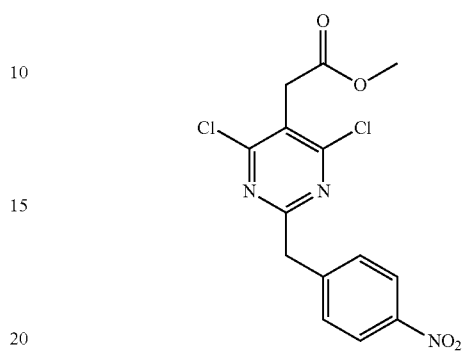

A 500 mL round bottom flask was charged with methyl [4,6-dihydroxy-2-(4-nitrobenzyl)pyrimidin-5-yl]acetate (7.62 g, 23.87 mmol), toluene (20 mL) and phosphoryl chloride (46 mL, 493 mmol). To this solution was slowly added N,N-dimethylaniline (17.1 mL, 134.9 mmol) giving a dark solution (caution: emission of smoke). After stirring for three hours under reflux (bath temperature: 130° C.) the mixture was allowed to cool to room temperature and volatiles were removed as far as possible under water aspirator vacuum at 50° C. The resulting black oil was dissolved in 120 mL ethyl acetate and slowly treated at 0° C. (ice bath cooling) with 40 mL saturated sodium hydrogen carbonate solution (caution: gas evolution, warming of the solution). After the aqueous phase was separated, the organic phase was successfully washed with additional 40 mL saturated sodium hydrogen carbonate solution, 30 mL water and 30 mL brine. The organic phase was dried over sodium sulfate and volatiles were removed under reduced pressure at 40° C. The crude product was purified by chromatography on silica gel on a 300×50 mm column using an ethyl acetate/n-heptane mixture (1:3, v/v) as eluent and thin layer chromatography as detecting unit (100 mL fractions). Fractions containing the desired product were pooled and the solvent was carefully removed under reduced pressure at about 40° C. giving an orange solid. Yield: 3.15 g (37.0%). Purity: 90% (GC). LC-MS: m/z=356.0 [(M+H)]$^+$.

Step 4: Synthesis of methyl [4,6-bis([$^2$H$_6$]dimethylamino)-2-(4-nitrobenzyl)pyrimidin-5-yl]acetate

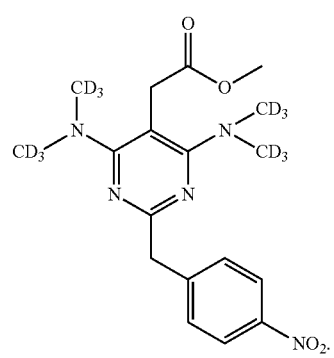 [SMILES: [2H]C([2H])([2H])N(c1nc(Cc2ccc([N+](=O)[O-])cc2)nc(N(C([2H])([2H])[2H])C([2H])([2H])[2H])c1CC(=O)OC)C([2H])([2H])[2H]]

A 30 mL long neck flask was charged with methyl [4,6-dichloro-2-(4-nitrobenzyl)pyrimidin-5-yl]acetate (1050 mg, 2.95 mmol, 90%) and [²H₆]dimethylamine hydrochloride (790 mg, 8.84 mmol, Aldrich 27, 946-3). At room temperature were added under stirring 1,3-dimethyltetrahydro-2-(1H)-pyrimidinone (8.0 mL, Aldrich 25, 156-9) and N,N-diisopropylethylamine (2.57 mL, 14.74 mmol, Aldrich D12580-6). The obtained dark purple solution was vigorously stirred at 85° C. for 40 minutes. Additional [²H₆]dimethylamine hydrochloride (258 mg, 2.75 mmol) and N,N-diisopropylethylamine (0.51 mL, 2.94 mmol) were added and the temperature was raised to 145° C. The reaction was monitored by HPLC showing after three hours stirring at 145° C. a product:unidentified side product:monosubstituted product of 9.4:3.4:3.4. After cooling to room temperature the reaction mixture was added to 50 mL water and the aqueous phase was extracted with ethyl acetate (8×10 mL). The combined organic phases were washed with 10 mL brine and dried over sodium sulfate. The solvent was carefully evaporated under water aspirator vacuum at 40° C. giving brown oil. For chromatographic purification the crude product was subjected to chromatography on silica gel on a 300×50 mm column using an ethyl acetate/n-heptane mixture (30:70, v/v) as eluent and thin layer chromatography as detecting unit (100 mL fractions). All fractions of methyl [4,6-bis([²H₆]dimethylamino)-2-(4-nitrobenzyl)pyrimidin-5-yl]acetate were pooled and the solvent was carefully removed under reduced pressure at about 40° C. giving an orange-brown gluey oil. Yield: 660 mg (54.6%). Purity 94% (HPLC). LC-MS: m/z=386.2 [(²H₁₂-M)+H]⁺.

Step 5: Synthesis of methyl [2-(4-aminobenzyl)-4,6-bis([²H₆]dimethyl-amino)pyrimidin-5-yl]acetate

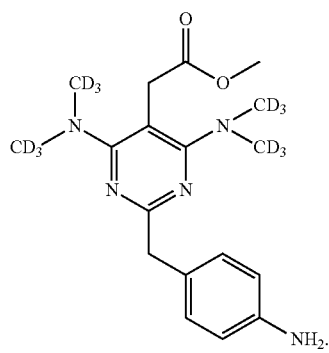

In a 250 mL round buttom flask, methyl [4,6-bis([²H₆]dimethylamino)-2-(4-nitrobenzyl)pyrimidin-5-yl]acetate (660 mg, 1.71 mmol) was dissolved methanol (20 mL). The catalyst palladium on charcoal (50 mg, 0.05 mmol, 10%) was added to the orange solution and the flask was purged with hydrogen for 10 minutes. After stirring for three hours under a hydrogen atmosphere using a 3 L balloon filled with hydrogen at room temperature a HPLC revealed complete conversion. The obtained light yellow solution was filtered over celite and the celite was washed with 30 mL methanol. The combined methanolic solutions were evaporated under reduced pressure at 40° C. giving a light brown gluey oil. Yield: 590 mg (93.2%). Purity 96% (GC). GC-MS: m/z=355 [(²H₁₂-M)]⁺.

Step 6: Synthesis of methyl [4,6-bis([²H₆]dimethylamino)-2-(4-{[4-(trifluoromethyl)benzoyl]amino}benzyl)pyrimidin-5-yl]acetate

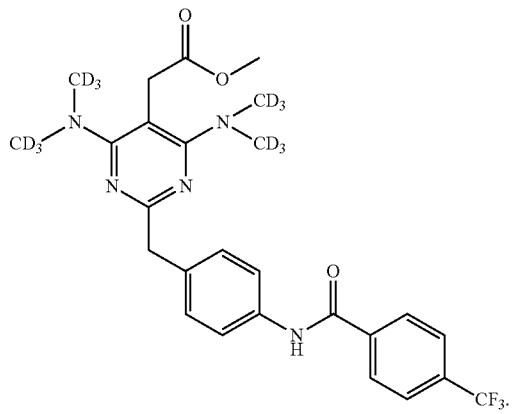 [SMILES: [2H]C([2H])([2H])N(c1nc(Cc2ccc(NC(=O)c3ccc(C(F)(F)F)cc3)cc2)nc(N(C([2H])([2H])[2H])C([2H])([2H])[2H])c1CC(=O)OC)C([2H])([2H])[2H]]

In a 250 mL round buttom flask methyl [2-(4-aminobenzyl)-4,6-bis([²H₆]dimethylamino)pyrimidin-5-yl]acetate (590 mg, 1.66 mmol, purity 96%) was dissolved in prior for use dried (over 10 g aluminum oxide, type 507C, Aldrich 19, 997-4) methylene chloride (15 mL, Merck 106044, >99.3%). After adding triethylamine (0.68 ml, 4.85 mmol) the mixture was cooled to 0° C. and 4-(trifluoromethyl)benzoyl chloride (0.30 mL, 2.00 mmol) dissolved in 1 mL methylene chloride was slowly added giving a yellow-orange solution. The mixture was stirred for 30 minutes at room temperature and after that time treated with 12 mL water. The organic phase was separated and the aqueous phase extracted with methylene chloride (3×5 mL). The pooled organic phases were dried over sodium sulfate and all volatiles were removed from the combined organic phases under water aspirator vacuum at 40° C. The crude product was purified by chromatography on silica gel on a 300×50 mm column using an ethyl acetate/n-heptane mixture (2:3, v/v) as eluent and thin layer chromatography as detecting unit (100 mL fractions). Fractions containing desired product were pooled and the solvent was carefully removed under reduced pressure at about 40° C. giving white microcrystalline solid. Yield: 1629: 770 mg (83.3%). Purity 91% (LC). LC-MS: m/z=528.2 [(²H₁₂-M)+H]⁺.

Step 7: Synthesis of 1

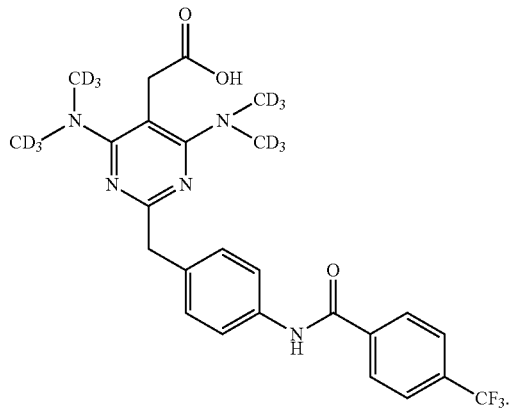 [SMILES: [2H]C([2H])([2H])N(c1nc(Cc2ccc(NC(=O)c3ccc(C(F)(F)F)cc3)cc2)nc(N(C([2H])([2H])[2H])C([2H])([2H])[2H])c1CC(=O)O)C([2H])([2H])[2H]]

In a 250 mL round bottom flask methyl [4,6-bis([²H₆]dimethylamino)-2-(4-{[4-(trifluoromethyl)benzoyl]amino}benzyl)pyrimidin-5-yl]acetate (770 mg, 1.46 mmol, 91%) was dissolved in 12.5 mL tetrahydrofuran (prior to use dried over aluminum oxide) and 4 mL methanol and 1N sodium hydroxide solution (4.48 mL, 4.48 mmol) was added at room temperature. After stirring under reflux (bath temperature 95° C.) for 90 minutes (HPLC, ratio product: educt=97:3), volatiles were removed under reduced pressure at 40° C. as far as possible. The residue was treated with 10 mL water. After extraction of the aqueous phase with 15 mL tert-butylmethylether (Merck 1.01845, 99.8%) roughly 5 mL 1N hydrochloric acid were added to the aqueous phase at 0° C. giving a white suspension (pH 6). After extraction with a tetrahydrofuran/ethyl acetate mixture (2:3, v/v, 10×8 mL) the suspension became clear. The combined organic phases were dried over sodium sulfate. The solvent was evaporated to dryness under reduced pressure at 40° C. leaving a light yellow solid behind. For chromatographic purification the crude product was subjected to chromatography on silica gel on a 400×50 mm column using a tetrahydrofuran/acetonitrile/acetic acid mixture (70:30:0.005, v/v) as eluent and thin layer chromatography as detecting unit (50 mL fractions). Fractions of 1 were pooled and the solvent was carefully removed under reduced pressure at about 40° C. giving a concentrated acetic acidic solution. After adding 300 mL water to this acetic acidic solution the obtained cloudy suspension was passed through a reversed phase cartridge C-18 (Phenomenex, 20 g). The product was washed out with tetrahydrofuran/acetonitrile mixture (v/v, 1:1). The solvent was removed under reduced pressure at 40° C. and the desired product was obtained as white microcrystalline solid. Total yield of 1: 606 mg (80.8%), purity 97.2%. LC-MS: m/z=514.2 [($^{2}H_{12}$-M)+H]$^{+}$.

Mass distribution: 98.7% (d-12), 1.3% (d-11). $^{1}$H NMR (400 MHz, DMSO-d$_{6}$): δ 12.04 (s, 1H, COOH), 10.39 (s, 1H, NH), 8.12 (d, 2H, CH), 7.91 (d, 2H, CH), 7.66 (d, 2H, CH), 7.32 (d, 2H, CH), 3.82 (s, 2H, CH$_{2}$), 3.42 (s, 2H, CH$_{2}$).

Example 2

[4,6-bis([$^{13}C_{2}$]dimethylamino)-2-(4-{[4-(trifluoromethyl)benzoyl]amino}benzyl)pyrimidin-5-yl]acetic acid (2)

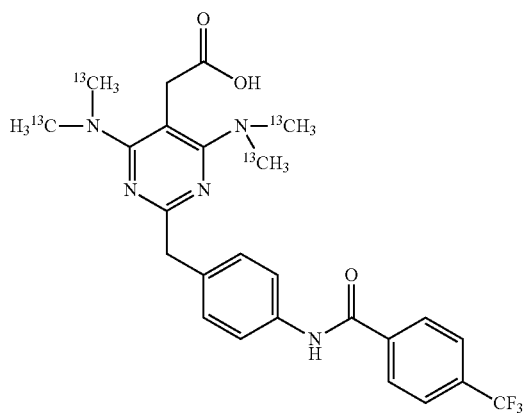 [SMILES: [13CH3]N([13CH3])c1nc(Cc2ccc(NC(=O)c3ccc(C(F)(F)F)cc3)cc2)nc(N([13CH3])[13CH3])c1CC(=O)O]

[4,6-bis([13C2]dimethylamino)-2-(4-{[4-(trifluoromethyl)benzoyl]amino}benzyl)pyrimidin-5-yl]acetic acid (2) is prepared following the synthesis described in Example 1 above, with the exception that [$^{13}C_{2}$]dimethylamine hydrochloride is used in Step 4 in place of [$^{2}H_{6}$]dimethylamine hydrochloride.

Example 3

[4,6-bis(dimethylamino)-2-(4-{[4-(trifluoromethyl)benzoyl]amino}benzyl)-[2-$^{13}$C]pyrimidin-5-yl]acetic acid (3)

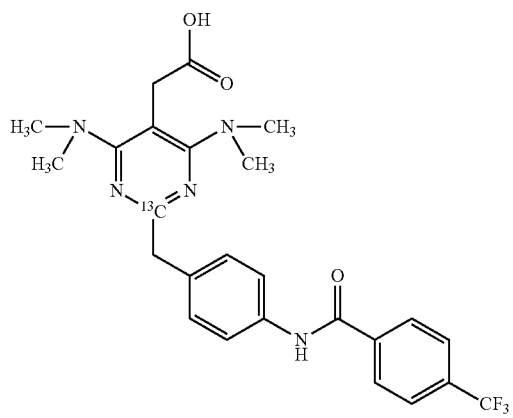 [SMILES: CN(C)c1n[13c](Cc2ccc(NC(=O)c3ccc(C(F)(F)F)cc3)cc2)nc(N(C)C)c1CC(=O)O]

[4,6-bis(dimethylamino)-2-(4-{[4-(trifluoromethyl)benzoyl]amino}benzyl)-[2-$^{13}$C]pyrimidin-5-yl]acetic acid (2) can be prepared in nine steps as follows.

Step 1: Synthesis of phenyl-[1-$^{13}$C]acetonitrile

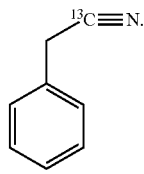

A 500 mL round bottom flask is charged with potassium [$^{13}$]cyanide and tetrabutylammonium bromide. After addition of methylene chloride, water (caution: H$^{13}$CN evolution possible!) and benzyl bromide, the phase-transfer reaction system is vigorously stirred overnight at room temperature. After this time, the organic phase is carefully separated from the aqueous phase (caution: H$^{13}$CN evolution possible!) and transferred on a column charged with sodium sulfate for drying. The aqueous phase is extracted with methylene chloride and the organic phase is transferred carefully on the sodium sulfate column. The column is rinsed with methylene chloride and the solvent is carefully removed under reduced pressure at 20° C. to yield crude product, which is purified by chromatography. For chromatographic purification, crude product is dissolved in methylene chloride and injected on a LiChrosorb® Si 60 column (40-63 μm, size C, 440×37 mm, Merck 1.10402) using an ethyl acetate/n-heptane mixture (1:4, v/v) as eluent at a flow rate of 20 mL/min. and a detection wavelength of 254 nm. The product elutes at these conditions between 25-30 minutes (attention: the product has a UV minimum around 254 nm!). The product fractions are combined and the solvent is carefully removed under reduced pressure at about 20° C. giving an almost colorless oil.

Step 2: Synthesis of (4-nitrophenyl)-[1-¹³C]acetonitrile

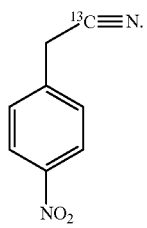

Caution: The following procedure requires purified phenyl-[1-¹³C]acetonitrile. Phenyl-[1-¹³C]acetonitrile is dissolved in methylene chloride and cooled to 0° C. At this temperature nitric acid dissolved in methylene chloride is quickly added resulting in a red, shortly boiling solution. After warming to room temperature and stirring for one hour the solution is diluted with methylene chloride and washed with a 10% sodium sulfate solution. The organic phase is dried on a column containing 10 g sodium sulfate. The column is rinsed with methylene chloride and the solvent is carefully evaporated under water aspirator vacuum at 40° C. The dried product can be dissolved in methylene chloride and purified by chromatopgraphy using a LiChrosorb® Si 60 column (40-63 µm, size C, 440×37 mm, Merck 1.10402) with an ethyl acetate/n-heptane mixture (1:4, v/v) as eluent at a flow rate of 20 mL/min. and a detection wavelength of 254 nm. Fractions containing desired product are pooled, the solvent removed under reduced pressure at about 40° C. and can be used in the next step without further purification. Main impurities are non-nitrated phenyl-[1-¹³C]acetonitrile and meta-nitrated (3-nitrophenyl)-[1-¹³C]acetonitrile.

Step 3: Synthesis of 2-(4-nitrophenyl)-[1-¹³C]ethanimidamide hydrochloride

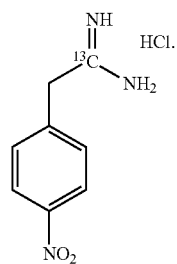

A suspension of (4-nitrophenyl)-[1-¹³C]acetonitrile in ethanol in a 250 mL round bottom flask is slowly treated at room temperature with 4N hydrochloric acid in dioxane and stirred for 22 hours. After careful removing the solvent under water aspirator vacuum at 40° C., the obtained wet pale yellow product is suspended in 24 mL ethanol. Then, a 7N ammonia solution in methanol is slowly added giving a pale gray suspension. After stirring for two hours additional 7N ammonia solution in methanol is added. After further stirring for 30 minutes at room temperature, all volatiles are removed under water aspirator vacuum at 40° C. To remove residues of ethanol and dioxane methyl t-butyl ether is added and once more all volatiles are removed under water aspirator vacuum at 40° C. The crude product is used without purification in the next step.

Step 4: Synthesis of methyl [4,6-dihydroxy-2-(4-nitrobenzyl)-[2-¹³C]pyrimidin-5-yl]acetate

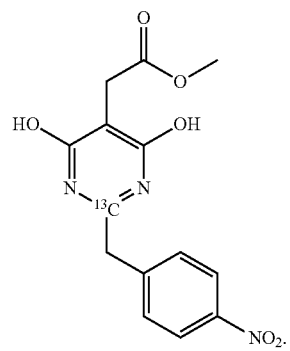

A 250 mL round bottom flask is charged with 2-(4-nitrophenyl)-[1-¹³C]ethanimidamide hydrochloride, triethyl ethane-1,1,2-tricarboxylate and methanol. To this solution is added a 25% sodium methoxide solution in methanol. After stirring for 30 minutes under reflux, additional 25% sodium methoxide solution in methanol is added. After further 30 minutes stirring under reflux, additional methanol can be added to gain a better stirring behavior. After a total time of 90 minutes stirring under reflux the mixture is cooled to 0° C. using an ice bath and carefully treated with 30 mL water. The mixture is slowly treated with 26 mL 6N hydrochloric acid producing a suspension. The suspension is stirred for additional 30 minutes and filtered to produce a solid, which can be washed with water. The product is dried in a desiccator under vacuum overnight. The crude product, barely soluble in most common solvents other than dimethylsulfoxide, can be used without purification in the next step.

Step 5: Synthesis of methyl [4,6-dichloro-2-(4-nitrobenzyl)-[2-¹³C]pyrimidin-5-yl]acetate

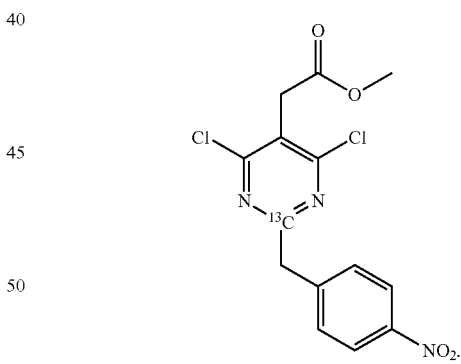

A 500 mL round bottom flask is charged with methyl [4,6-dihydroxy-2-(4-nitrobenzyl)-[2-¹³C]pyrimidin-5-yl]acetate, toluene and phosphoryl chloride (caution: heating of the solution possible due to wet starting material). To this solution is slowly added N,N-dimethylaniline (caution: emission of smoke). After stirring for two hours under reflux (bath temperature: 120° C.) the mixture is allowed to cool to room temperature and all volatiles are removed as far as possible under water aspirator vacuum at 50° C. The resulting black oil is dissolved in ethyl acetate and slowly treated at 0° C. (ice bath cooling) with saturated sodium hydrogen carbonate solution. After the aqueous phase is separated, the organic phase can be successively washed with saturated sodium hydrogen carbonate solution, water and brine. The combined aqueous phases are re-extracted with ethyl acetate and the pooled organic phases are dried over a sodium sulfate column. The column is rinsed with ethyl acetate and volatiles are removed under reduced pressure at 40° C. In addition to desired product, the corresponding pyrimidinyl acetic acid may be present. To convert the acid to the desired ester, the crude product is refluxed (bath temperature: 120° C.) with thionyl chloride for 30 minutes. After removing excess of thionyl chloride at reduced pressure at 40° C., the residue is carefully treated with methanol at 5° C. Volatiles are removed under water aspirator vacuum at 20° C. For chromatographic purification, the crude product can be dissolved in methylene chloride and injected, in batches for separate runs, on a LiChrosorb® Si 60 column (40-63 μm, size C, 440×37 mm, Merck 1.10402) using an ethyl acetate/n-heptane mixture (1:4, v/v) as eluent at a flow rate of 20 mL/min. and a detection wavelength of 254 nm. Desired product should elute at these conditions between 70-95 minutes. Fractions of desired product are pooled and the solvent carefully removed under reduced pressure at about 40° C.

Step 6: Synthesis of methyl [4,6-bis(dimethylamino)-2-(4-nitrobenzyl)-[2-$^{13}$C]pyrimidin-5-yl]acetate

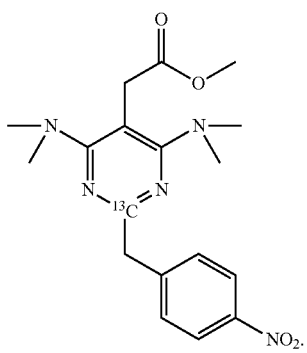 [SMILES: COC(=O)Cc1c(N(C)C)n[13c](Cc2ccc([N+](=O)[O-])cc2)nc1N(C)C]

To solid methyl [4,6-dichloro-2-(4-nitrobenzyl)-[2-$^{13}$C]pyrimidin-5-yl]acetate and dimethylamine hydrochloride in a 20 mL long neck flask are added at room temperature 1,3-dimethyltetrahydro-2-(1H)-pyrimidinone ("DMPU") and N,N-diisopropyl-ethylamine. (Note: this procedure may not work when the starting solid is pre-dissolved in DMPU). The solution is vigorously stirred at 85° C. for 30 minutes. Additional dimethylamine hydrochloride and N,N-diisopropyl-ethylamine are added and the temperature is raised to 150° C. and stirred for about four hours. The reaction can be monitored by HPLC. After cooling to room temperature, the reaction mixture is added to 60 mL water and the aqueous phase is extracted with ethyl acetate. The combined organic phases are washed with brine and the combined aqueous phases can be re-extracted with ethyl acetate. The pooled organic phases are dried on a column containing sodium sulfate and magnesium sulfate. The column is rinsed with ethyl acetate and the solvent is carefully evaporated under water aspirator vacuum at 40° C. For chromatographic purification, the crude product is dissolved in methylene chloride and injected on a LiChrosorb® Si 60 column using an ethyl acetate/n-heptane mixture (28:72, v/v) as eluent at a flow rate of 15 mL/min with a detection wavelength of 254 nm. Fractions of desired product are pooled and the solvent is carefully removed under reduced pressure at about 40° C.

Step 7: Synthesis of methyl [2-(4-aminobenzyl)-4,6-bis(dimethylamino)-[2-$^{13}$C]pyrimidin-5-yl]acetate

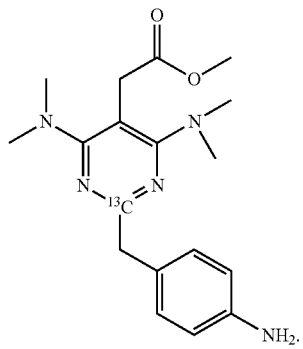 [SMILES: COC(=O)Cc1c(N(C)C)n[13c](Cc2ccc(N)cc2)nc1N(C)C]

In a 250 mL round buttom flask methyl [4,6-bis(dimethylamino)-2-(4-nitrobenzyl)-[2-$^{13}$C]pyrimidin-5-yl]acetate is dissolved in methanol. The catalyst palladium on charcoal is added to the solution and the flask is purged with hydrogen for 10 minutes. Stir for three hours under a hydrogen atmosphere using a 3 L balloon filled with hydrogen at room temperature. HPLC can be used to verify complete conversion. The resulting light yellow solution is filtered over celite and the celite is washed with methanol. The combined methanolic solutions are evaporated under reduced pressure at 40° C. giving a light brown gluey oil.

At this stage it is possible to separate the desired para-substituted compound from the meta-substituted side product that results from the nitration described in Step 2, above. Crude product is dissolved in an n-heptane:ethyl acetate:triethylamine (1:1:0.001, v/v/v) mixture and for chromatographic purification the solution is injected on a LiChrosorb® Si 60 column using an n-heptane:ethyl acetate:triethylamine (1:1:0.001, v/v/v) mixture as eluent for 75 minutes followed by an n-heptane:ethyl acetate:triethylamine (1:3:0.001, v/v/v) mixture for 20 minutes at a flow rate of 15 mL/min. and a detection wavelength of 254 nm. Before loading sample, the column was calibrated 30 minutes with the n-heptane:ethyl acetate:triethylamine (1:1:0.001, v/v/v) mixture. Fractions of desired product are pooled and the solvent carefully removed under reduced pressure at about 40° C.

Step 8: Synthesis of methyl [4,6-bis(dimethylamino)-2-(4-{[4-(trifluoromethyl)benzoyl]amino}benzyl)[2-$^{13}$C]pyrimidin-5-yl]acetate

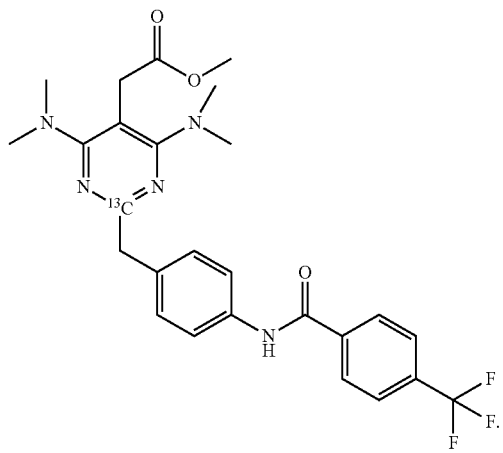 [SMILES: COC(=O)Cc1c(N(C)C)n[13c](Cc2ccc(NC(=O)c3ccc(C(F)(F)F)cc3)cc2)nc1N(C)C]

In a 250 mL round buttom flask methyl [2-(4-aminobenzyl)-4,6-bis(dimethylamino)-[2-$^{13}$C]pyrimidin-5-yl]acetate is dissolved in methylene chloride. After adding triethylamine, the mixture is cooled to 0° C. and 4-(trifluoromethyl)benzoyl chloride dissolved in methylene chloride is slowly added. The mixture is stirred for one hour at room temperature and after that time treated with water. The organic phase is separated and the aqueous phase extracted with methylene chloride. The pooled organic phases are dried on a column containing 10 g sodium sulfate. After the column is rinsed with 20 mL methylene chloride volatiles are removed from the combined organic phases under water aspirator vacuum at 40° C. For chromatographic purification, the obtained crude product is dissolved in methylene chloride and injected on a LiChrosorb® Si 60 column using an n-heptane:ethyl acetate (63:27, v/v) mixture as eluent at a flow rate of 15 mL/min and a detection wavelength of 254 nm. Fractions containing desired product can be pooled and the solvent carefully removed under reduced pressure at about 40° C. to yield product as a solid.

Step 9: Synthesis of [4,6-bis(dimethylamino)-2-(4-{[4-(trifluoromethyl)benzoyl]amino}benzyl)-[2-$^{13}$C]pyrimidin-5-yl]acetic acid (3)

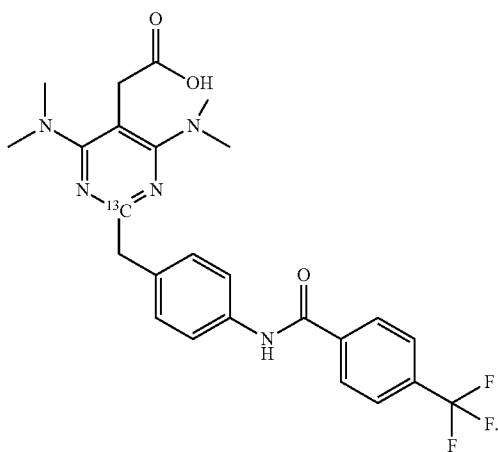 [SMILES: CN(C)c1n[13c](Cc2ccc(NC(=O)c3ccc(C(F)(F)F)cc3)cc2)nc(N(C)C)c1CC(=O)O]

[4,6-bis(dimethylamino)-2-(4-{[4-(trifluoromethyl)benzoyl]amino}benzyl)-[2-$^{13}$C]pyrimidin-5-yl]acetate is dissolved in tetrahydrofuran, methanol and 1N sodium hydroxide solution at room temperature. After stirring under reflux (bath temperature 95° C.) for 90 minutes, volatiles are removed under reduced pressure at 40° C. as far as possible. To the residue are added water and sodium hydroxide. After extraction of the aqueous phase with tert-butylmethylether, 1N hydrochloric acid is added to the aqueous phase at 0° C. to give a white suspension (pH 6). After extraction with a tetrahydrofuran/ethyl acetate mixture (22:78, v/v, 10×15 mL) the suspension should become clear (pH 7-8). Additional 1N hydrochloric acid is added to the aqueous phase (pH 5) followed by further extraction with a tetrahydrofuran/ethyl acetate mixture (22:78, v/v, 5×15 mL) until HPLC of the aqueous phase reveals no more product. The combined organic phases can be dried over 50 g sodium sulfate (KMF KMF.03-020) followed by a sodium sulfate (15 g) column. The column is rinsed with a tetrahydrofuran/ethyl acetate mixture (22:78, v/v). The solvent is evaporated to dryness under reduced pressure at 40° C. to leave solid crude product. The crude product is suspended in an acetonitrile/tetrahydrofuran mixture (95:5, v/v) and the suspension is added on a cartridge SI60 (Varian, 10 g). The cartridge is rinsed with 20 mL of an acetonitrile/tetrahydrofuran mixture (95:5, v/v) to elute side products (control by HPLC). The product 3, is eluted with 250 mL of an acetonitrile/tetrahydrofuran/acetic acid mixture (60:40:0.1). After evaporation to dryness, 3 can be recrystallized from 130 mL methanol. After standing for two days at −20° C., white microcrystalline 3 can be obtained, filtered off and washed with 25 mL cold methanol. By drying over aluminum oxide and immediately dissolved in tetrahydrofuran, compound 3 can be characterized by UV, TLC, HPLC, NMR or mass spectrometry.

Compounds provided herein can be prepared to have $^{14}$C in place of $^{13}$C by following the synthetic procedures described herein using $^{14}$C in place of $^{13}$C labeled starting materials.

Example 4

Pharmacokinetics, Bioavailability and Inhibitory Activity of [4,6-bis([$^2$H$_6$]dimethylamino)-2-(4-{[4-(trifluoromethyl)benzoyl]amino}benzyl)pyrimidin-5-yl]acetic acid (1)

The pharmacokinetics and bioavailability of [4,6-bis([$^2$H$_6$]dimethylamino)-2-(4-{[4-(trifluoromethyl)benzoyl]amino}benzyl)pyrimidin-5-yl]acetic acid (1) and [4,6-bis-dimethylamino)-2-(4-{[4-(trifluoromethyl)benzoyl]amino}benzyl)pyrimidin-5-yl]acetic acid ("the undeuterated analog") were compared in male Han Wistar rats after intravenous ("IV") and oral ("PO") administration.

The following additional acronyms and definitions are used in the study:

AUC0-∞—area under the plasma concentration time curve from time 0 to infinity
AUC0-t—area under the plasma concentration time curve from time 0 to the last quantifiable timepoint
AUMC—area under the first moment curve
CL—total plasma clearance
Cmax—maximum plasma concentration
MRT—mean residence time
PEG—polyethylene glycol
t½—elimination half-life
tmax—time of maximum plasma concentration
Vss—steady-state volume of distribution Compound 1 (1.02 mg/kg) and the undeuterated analog (1.0 mg/kg) and were administered simultaneously as a solution in PEG 400:ethanol:water (40:10:50) both intravenously and orally (by gavage) to four male rats per dose route. The doses were equivalent on a molar basis. Blood samples were collected serially up to 48 h postdose. Plasma concentrations of each compound were measured by an LC/MS/MS method with a lower limit of quantitation ("LLOQ") of 1.00 ng/mL for both analytes (1.99 nM for the reference compound and 1.95 nM for 1). Noncompartmental pharmacokinetic parameters were calculated and the results compared statistically using paired t-tests, since the simultaneous administration of both compounds allows each rat to serve as its own control.

The plasma concentrations of 1 were greater than those of the undeuterated analog in every time point of every rat in both dose routes.

After IV administration, the AUC$_{0-\infty}$ of 1 was 28% higher that that of the undeuterated analog. The clearance was 80% that of the undeuterated analog. These differences were statistically significant (p<0.05). In addition, the increase in mean residence time ("MRT") of the deuterated analog was marginally significant (p=0.061).

After PO administration, the AUC$_{0-t}$ of 1 was 71% higher that that of the undeuterated analog. This difference was statistically significant (p<0.05). In addition, C$_{max}$ and AUC$_{0-\infty}$ of 1 were 42% and 63% higher than the corresponding values for the undeuterated analog. However, these values were only marginally significant (p=0.066 and p=0.053, respectively). The larger increase in AUC after PO dosing compared to IV dosing appeared to be due to greater bioavailability of the deuterated analog; the values were 52.5% and 45.6% for 1 and the undeuterated analog, respectively. This difference was statistically significant (p<0.01).

The pharmacokinetics of 1 showed both reduced clearance and better bioavailability relative to the unlabeled drug.

The pharmacokinetic parameters determined for this study are presented in the tables below:

Summary of Mean (±SD) Pharmacokinetic Parameters for Compound 1 ("D") and the Undeuterated Analog ("H") in Male Han Wistar Rats after Simultaneous Intravenous Administration of the Respective Free Acids

| Dose Route | Intravenous | | |
|---|---|---|---|
| N | 4 | | |
| Pharmacokinetic parameter | D | H | D/H ratio |
| Dose (mg/kg) | 1.02 | 1 | 1[a] |
| CL (mL/min/kg) | 1.73 ± 0.809[b] | 2.17 ± 1.07 | 0.799 ± 0.0192 |
| $V_{SS}$ (L/kg) | 0.170 ± 0.090 | 0.186 ± 0.101 | 0.921 ± 0.109 |
| $t_{1/2}^{c}$ (h)[d] | 4.63 ± 1.62 | 3.23 ± 1.99 | 1.42 ± 0.471 |
| MRT (h) | 1.80 ± 0.916 | 1.62 ± 0.861 | 1.16 ± 0.160 |
| $C_{max}$ (nM) | — | — | — |
| $t_{max}$ (h) | — | — | — |
| $AUC_{0-t}$ (nM·h) | 22,600 ± 8,810 | 17,800 ± 7,280[b] | 1.28 ± 0.0332 |
| $AUC_{0-\infty}$ (nM·h)[c] | 22,600 ± 8,200 | 17,900 ± 7,270[b] | 1.28 ± 0.0302 |
| Bioavailability (%) | — | — | — |

[a]On a molar basis.
[b]p < 0.05 compared to deuterated compound (paired t-test)
[c]CL/F
[d]Harmonic mean.
[e]Median and range.

Summary of Mean (±SD) Pharmacokinetic Parameters for Compound 1 ("D") and the Undeuterated Analog ("H") in Male Han Wistar Rats after Simultaneous Oral Administration of the Respective Free Acids

| Dose Route | Oral | | |
|---|---|---|---|
| N | 4 | | |
| Pharmacokinetic parameter | D | H | D/H ratio |
| Dose (mg/kg) | 1.02 | 1 | 1[a] |
| CL (mL/min/kg) | 4.93[c] ± 3.99 | 8.97[c] ± 8.78 | 0.627 ± 0.105 |
| $V_{SS}$ (L/kg) | — | — | — |
| $t_{1/2}^{c}$ (h)[d] | 1.82 ± 0.976 | 2.39 ± 2.11 | 0.734 ± 0.341 |
| MRT (h) | 2.61 ± 0.708 | 3.12 ± 1.21 | 0.906 ± 0.260 |
| $C_{max}$ (nM) | 4,260 ± 3,220 | 3,080 ± 2,390 | 1.42 ± 0.0989 |
| $t_{max}$ (h) | 0.5 (0.5-1.0)[e] | 0.5 (0.5-1.0)[e] | 1.00 ± 0.00 |
| $AUC_{0-t}$ (nM·h) | 11,800 ± 10,300[b] | 8,070 ± 7,950 | 1.71 ± 0.467 |
| $AUC_{0-\infty}$ (nM·h)[c] | 11,900 ± 10,300 | 8,160 ± 7,880 | 1.63 ± 0.303 |
| Bioavailability (%) | 52.5 ± 45.3[b] | 45.6 ± 44.0 | 1.29 ± 0.240 |

[a]On a molar basis.
[b]p < 0.05 compared to deuterated compound (paired t-test)
[c]CL/F
[d]Harmonic mean.
[e]Median and range.

Individual and mean plasma concentrations expressed in mass units and molar units after intravenous and oral administration are presented in the tables below:

Individual and Mean Plasma Concentrations (Mass Units) of 1 and the Undeuterated Analog in Male Han Wistar Rats after Simultaneous Intravenous Administration of 1 (1.02 mg/kg) and the Undeuterated Analog (1 mg/kg)

| Time (h) | 1 | 2 | 3 | 4 | Mean | SD |
|---|---|---|---|---|---|---|
| Undeuterated Analog Plasma Concentrations (ng/mL) | | | | | | |
| 0.03 | 136,000[a] | 15,800 | 24,600 | 13,700 | 47,500 | 59,200 |
| 0.25 | 5,890 | 7,660 | 11,500 | 3,430 | 7,120 | 3,400 |
| 0.5 | 3,430 | 4,670 | 5,510 | 62,900 | 19,100[a] | 29,200 |
| 1 | 1,380 | 2,290 | 2,080 | 681 | 1,610 | 730 |
| 2 | NS | 901 | 741 | 128 | 590 | 408 |
| 4 | 175 | 365 | 170 | 46.9 | 189 | 131 |
| 6 | 105 | 253 | 81.3 | 24.2 | 116 | 98 |
| 8 | 64.0 | 173 | 88.4 | 12.0 | 84.4 | 67.1 |
| 24 | 12.0 | 4.78 | 3.29 | <1.00 | 5.02 | 5.07 |
| 48 | 1.01 | <1.00 | <1.00 | <1.00 | 0.253 | 0.505 |
| Compound 1 Plasma Concentrations (ng/mL) | | | | | | |
| 0.03 | 168,000[a] | 20,000 | 31,200 | 17,500 | 59,200 | 72,800 |
| 0.25 | 7,430 | 9,800 | 14,200 | 4460 | 8,970 | 4,110 |
| 0.5 | 4,440 | 6,030 | 6,890 | 80,300 | 24,400[a] | 37,300 |
| 1 | 1,830 | 3,000 | 2,800 | 949 | 2140 | 947 |
| 2 | NS | 1,190 | 940 | 184 | 771 | 524 |
| 4 | 228 | 459 | 237 | 66.4 | 248 | 161 |
| 6 | 140 | 326 | 107 | 34.7 | 152 | 124 |
| 8 | 88.2 | 216 | 115 | 18.4 | 109 | 81.9 |
| 24 | 20.6 | 6.70 | 4.54 | 1.49 | 8.33 | 8.45 |
| 48 | 1.97 | 1.40 | <1.00 | <1.00 | 0.843 | 1.00 |

[a]Sample excluded from the mean plasma concentrations and not used in the PK calculations.
NS—No sample collected Individual and Mean Plasma Concentrations (Molar Units) of 1 and the Undeuterated Analog in Male Han Wistar Rats after Simultaneous Intravenous Administration of 1 (1.02 mg/kg) and the Undeuterated Analog (1 mg/kg)

| Time (h) | 1 | 2 | 3 | 4 | Mean | SD |
|---|---|---|---|---|---|---|
| Undeuterated Analog Plasma Concentrations (nM) | | | | | | |
| 0.03 | 271,000[a] | 31,500 | 49,100 | 27,300 | 94800 | 118,000 |
| 0.25 | 11,700 | 15,300 | 22,900 | 6,840 | 14200 | 6,770 |
| 0.5 | 6,840 | 9,310 | 11,000 | 125,000 | 38100[a] | 58,200 |
| 1 | 2,750 | 4,570 | 4,150 | 1,360 | 3210 | 1,460 |
| 2 | NS | 1,800 | 1,480 | 255 | 1180 | 814 |
| 4 | 349 | 728 | 339 | 93.5 | 377 | 262 |
| 6 | 209 | 504 | 162 | 48.3 | 231 | 194 |
| 8 | 128 | 345 | 176 | 23.9 | 168 | 134 |
| 24 | 23.9 | 9.53 | 6.56 | <1.99 | 10.0 | 10.1 |
| 48 | 2.01 | <1.99 | <1.99 | <1.99 | 0.503 | 1.01 |
| Compound 1 Plasma Concentrations (nM) | | | | | | |
| 0.03 | 327,000[a] | 38,900 | 60,800 | 34,100 | 115000 | 142000 |
| 0.25 | 14,500 | 19,100 | 27,700 | 8,690 | 17500 | 8010 |
| 0.5 | 8,650 | 11,700 | 13,400 | 156,000 | 47500[a] | 72600 |
| 1 | 3,560 | 5,840 | 5,450 | 1,850 | 4180 | 1840 |
| 2 | NS | 2,320 | 1,830 | 358 | 1500 | 1020 |
| 4 | 444 | 894 | 462 | 129 | 482 | 314 |
| 6 | 273 | 635 | 208 | 67.6 | 296 | 242 |
| 8 | 172 | 421 | 224 | 35.8 | 213 | 160 |
| 24 | 40.1 | 13.0 | 8.84 | 2.90 | 16.2 | 16.5 |
| 48 | 3.84 | 2.73 | <1.95 | <1.95 | 1.64 | 1.95 |

[a]Sample excluded from the mean plasma concentrations and not used in the PK calculations.
NS—No sample collected Individual and Mean Plasma Concentrations (Mass Units) of 1 and the Undeuterated Analog in Male Han Wistar Rats after Simultaneous Oral Administration of 1 (1.02 mg/kg) and the Undeuterated Analog (1.01 mg/kg)

| Time (h) | 1 | 2 | 3 | 4 | Mean | SD |
|---|---|---|---|---|---|---|
| Undeuterated Analog Plasma Concentrations (ng/mL) | | | | | | |
| 0.25 | 959 | 308 | 1,520 | 1,180 | 992 | 511 |
| 0.5 | 1,060 | 355 | 2,940 | 1,590 | 1,490 | 1,090 |
| 1 | 744 | 191 | 3,180 | 1,220 | 1,330 | 1,300 |
| 2 | 463 | 104 | 1,290 | 548 | 601 | 498 |
| 4 | 68.4 | 32.5 | 559 | 178 | 209 | 241 |
| 6 | 22.0 | 24.1 | 387 | 93.3 | 132 | 173 |
| 8 | 12.3 | 18.7 | 217 | 76.8 | 81.2 | 95.1 |
| 24 | <1.00 | <1.00 | 2.99 | 2.16 | 1.29 | 1.52 |
| 48 | <1.00 | <1.00 | 1.57 | 1.57 | 0.393 | 0.79 |
| Compound 1 Plasma Concentrations (ng/mL) | | | | | | |
| 0.25 | 1,290 | 466 | 2,110 | 1,660 | 1,380 | 696 |
| 0.5 | 1,510 | 571 | 3,970 | 2,210 | 2,070 | 1,440 |
| 1 | 1,100 | 432 | 4,450 | 1,830 | 1,950 | 1,760 |
| 2 | 731 | 349 | 1,950 | 972 | 1,000 | 683 |
| 4 | 137 | 147 | 759 | 329 | 343 | 291 |
| 6 | 37.6 | 37.8 | 535 | 138 | 187 | 237 |
| 8 | 20.2 | 27.6 | 289 | 109 | 111 | 125 |
| 24 | <1.00 | <1.00 | 4.01 | 3.46 | 1.87 | 2.17 |
| 48 | <1.00 | <1.00 | <1.00 | <1.00 | 0.00 | 0.00 |

NS—No sample collected

Individual and Mean Plasma Concentrations (Molar Units) of 1 and the Undeuterated Analog in Male Han Wistar Rats after Simultaneous Oral Administration of 1 (1.02 mg/kg) and the Undeuterated Analog (1.01 mg/kg)

| Time (h) | 1 | 2 | 3 | 4 | Mean | SD |
|---|---|---|---|---|---|---|
| Undeuterated Analog Plasma Concentrations (nM) | | | | | | |
| 0.25 | 1,910 | 614 | 3,030 | 2,350 | 1980 | 1020 |
| 0.5 | 2,110 | 708 | 5,860 | 3,170 | 2960 | 2180 |
| 1 | 1,480 | 381 | 6,340 | 2,430 | 2660 | 2590 |
| 2 | 923 | 207 | 2,570 | 1,090 | 1200 | 993 |
| 4 | NS | 64.8 | 1,120 | 355 | 511 | 542 |
| 6 | 43.9 | 48.1 | 772 | 186 | 262 | 346 |
| 8 | 24.5 | 37.3 | 433 | 153 | 162 | 190 |
| 24 | <1.99 | <1.99 | 5.96 | 4.31 | 2.57 | 3.04 |
| 48 | <1.99 | <1.99 | <1.99 | 3.13 | 0.783 | 1.57 |
| Compound 1 Plasma Concentrations (nM) | | | | | | |
| 0.25 | 2,510 | 907 | 4,110 | 3,230 | 2,690 | 1,360 |
| 0.5 | 2,940 | 1,110 | 7,730 | 4,300 | 4,020 | 2,800 |
| 1 | 2,140 | 841 | 8,670 | 3,560 | 3,800 | 3,430 |
| 2 | 1,420 | 680 | 3,800 | 1,890 | 1,950 | 1,330 |
| 4 | 267 | 286 | 1,480 | 641 | 668 | 567 |
| 6 | 73.2 | 73.6 | 1,040 | 269 | 364 | 461 |
| 8 | 39.3 | 53.7 | 563 | 212 | 217 | 243 |
| 24 | <1.95 | <1.95 | 7.81 | 6.74 | 3.64 | 4.22 |
| 48 | <1.95 | <1.95 | <1.95 | <1.95 | 0.00 | 0.00 |

NS—No sample collected

Individual and Mean Pharmacokinetic Parameters for 1 ("D") and the Undeuterated Analog ("H") in Male Han Wistar Rats after Simultaneous Intravenous Administration of 1 (1.02 mg/kg) and the Undeuterated Analog (1.01 mg/kg)

| Pharmacokinetic Parameter | Isotope | Rat Number | | | | Statistic | |
|---|---|---|---|---|---|---|---|
| | | 1 | 2 | 3 | 4 | Mean | SD |
| Body Weight (g) | — | 230 | 230 | 205 | 230 | 224 | 12.5 |
| AUC$_{0-t}$ (nM·h) | D | 19,000 | 29,300 | 30,300 | 11,900 | 22,600 | 8,810 |
| | H | 14,700 | 23,300 | 24,300 | 9,020 | 17,800 | 7,280 |
| | D/H ratio | 1.29 | 1.26 | 1.25 | 1.32 | 1.28 | 0.0332 |
| AUC$_{0-\infty}$ (nM·h)$^a$ | D | 19,000 | 29,400 | 30,300 | 11,900 | 22,600 | 8,820 |
| | H | 14,700 | 23,300 | 24,400 | 9,090 | 17,900 | 7,270 |
| | D/H ratio | 1.29 | 1.26 | 1.24 | 1.31 | 1.28 | 0.0302 |
| CL (mL/min/kg) | D | 1.78 | 1.15 | 1.12 | 2.85 | 1.73 | 0.809 |
| | H | 2.25 | 1.43 | 1.36 | 3.66 | 2.17 | 1.07 |
| | D/H ratio | 0.791 | 0.804 | 0.824 | 0.779 | 0.799 | 0.0192 |
| Vss (L/kg) | D | 0.297 | 0.162 | 0.0868 | 0.135 | 0.170 | 0.090 |
| | H | 0.328 | 0.189 | 0.103 | 0.125 | 0.186 | 0.101 |
| | D/H ratio | 0.905 | 0.857 | 0.843 | 1.08 | 0.921 | 0.109 |
| t$_{1/2}$ (h) | D | 7.28 | 4.79 | 3.62 | 4.12 | 4.63$^b$ | 1.62 |
| | H | 6.68 | 3.12 | 3.60 | 2.03 | 3.23$^b$ | 1.99 |
| | D/H ratio | 1.09 | 1.54 | 1.01 | 2.03 | 1.42 | 0.471 |
| MRT (h) | D | 2.77 | 2.34 | 1.30 | 0.788 | 1.80 | 0.916 |
| | H | 2.43 | 2.20 | 1.26 | 0.569 | 1.62 | 0.861 |
| | D/H ratio | 1.14 | 1.06 | 1.03 | 1.38 | 1.16 | 0.160 |

$^a$Extrapolated area averaged <0.15 and <0.35% of total area for deuterated and undeuterated compound, respectively.
$^b$Mean half-life is harmonic mean.

Individual and Mean Pharmacokinetic Parameters for 1 ("D") and the Undeuterated Analog ("H") in Male Han Wistar Rats after Simultaneous Oral Administration of 1 (1.02 mg/kg) and the Undeuterated Analog (1.01 mg/kg)

| Pharmacokinetic Parameter | Isotope | Rat Number | | | | Statistic | |
|---|---|---|---|---|---|---|---|
| | | 1 | 2 | 3 | 4 | Mean | SD |
| Body Weight (g) | — | 220 | 260 | 220 | 250 | 238 | 20.6 |
| C$_{max}$ (nM) | D | 2,940 | 1,110 | 8,670 | 4,300 | 4,260 | 3,220 |
| | H | 2,110 | 708 | 6,340 | 3,170 | 3,080 | 2,390 |
| | D/H ratio | 1.39 | 1.57 | 1.37 | 1.36 | 1.42 | 0.0989 |
| t$_{max}$ (h) | D | 0.5 | 0.5 | 1 | 0.5 | 0.5$^a$ | (0.5-1)$^b$ |
| | H | 0.5 | 0.5 | 1 | 0.5 | 0.5$^a$ | (0.5-1)$^b$ |
| | D/H ratio | 1.00 | 1.00 | 1.00 | 1.00 | 1.00 | 0.00 |
| AUC$_{0-t}$ (nM·h) | D | 6,190 | 3,070 | 26,300 | 11,700 | 11,800 | 10,300 |
| | H | 3,880 | 1,280 | 19,300 | 7,820 | 8,070 | 7,950 |
| | D/H ratio | 1.60 | 2.40 | 1.36 | 1.50 | 1.71 | 0.467 |
| AUC$_{0-\infty}$ (nM·h)$^c$ | D | 6,260 | 3,190 | 26,300 | 11,700 | 11,900 | 10,300 |
| | H | 3,920 | 1,550 | 19,300 | 7,850 | 8,160 | 7,880 |
| | D/H ratio | 1.60 | 2.06 | 1.36 | 1.49 | 1.63 | 0.303 |
| CL/F (mL/min/kg) | D | 5.29 | 10.4 | 1.26 | 2.82 | 4.93 | 3.99 |
| | H | 8.48 | 21.5 | 1.72 | 4.23 | 8.97 | 8.78 |
| | D/H ratio | 0.624 | 0.484 | 0.733 | 0.667 | 0.627 | 0.105 |
| MRT (h) | D | 1.68 | 2.45 | 3.30 | 3.00 | 2.61 | 0.708 |
| | H | 1.40 | 4.25 | 3.36 | 3.47 | 3.12 | 1.21 |
| | D/H ratio | 1.20 | 0.576 | 0.982 | 0.865 | 0.906 | 0.260 |
| t$_{1/2}$ (h) | D | 1.13 | 1.61 | 2.57 | 3.32 | 1.82$^d$ | 0.976 |
| | H | 1.10 | 5.02 | 2.57 | 5.63 | 2.39$^d$ | 2.11 |
| | D/H ratio | 1.03 | 0.32 | 1.00 | 0.59 | 0.734 | 0.341 |
| Bioavailability (%) | D | 13.3 | 6.79 | 56.0 | 24.9 | 25.2 | 21.8 |
| | H | 10.3 | 4.06 | 50.5 | 20.6 | 21.3 | 20.6 |
| | D/H ratio | 1.30 | 1.67 | 1.11 | 1.21 | 1.32 | 0.246 |

$^a$Median
$^b$Range
$^c$Extrapolated area averaged <1.5 and <5% of total area for deuterated and undeuterated compound, respectively.
$^d$Mean half-life is harmonic mean.

Applicants have also found that compound 1 has comparable biological inhibitory activity in vitro compared to the undeuterated analog. The result suggests that the in vivo biological inhibitory activity of compound 1 will be similar to the undeuterated analog, when compared at similar plasma levels or systemic exposure.

The examples set forth above are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the art are intended to be within the scope of the following claims. All publications, patents, and patent applications cited in this specification are incorporated herein by reference as if each such publication, patent, or patent application were specifi- It is claimed:

1. An isotopically enriched compound of formula I:

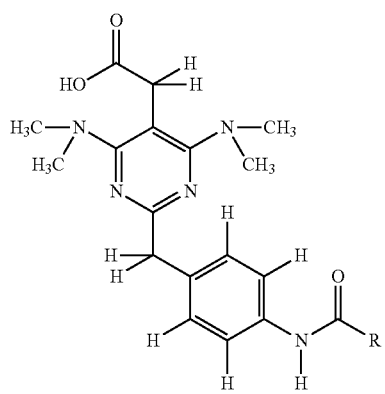

I or pharmaceutically acceptable salt thereof,
wherein
R is hydrogen, $C_{1-6}$ alkyl, $C_{3-8}$ cycloalkyl optionally substituted by $C_{1-6}$ alkyl, or phenyl optionally substituted with 1-4 substituents selected from halogen, $C_{1-4}$ alkyl optionally substituted with mono-, di- or tri- halogen, and $C_{1-4}$ alkoxy; and wherein
one or more hydrogen atoms are replaced by a deuterium atom or
one or more carbon atoms are replaced by a carbon-13 atom.

2. The compound of claim 1, wherein R is phenyl.

3. The compound of claim 1 of the formula III:

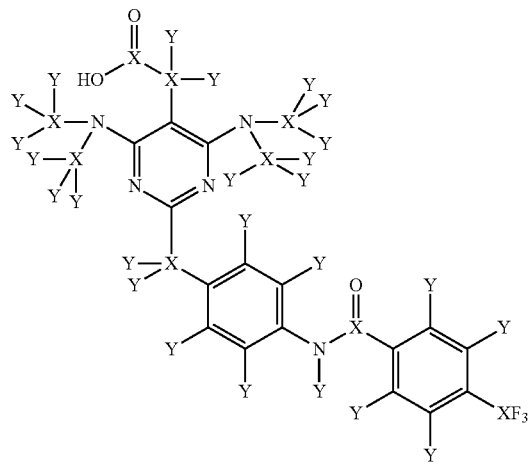

III wherein
each Y atom is a hydrogen atom or deuterium atom; and
each X atom is a carbon-12 atom or carbon-13 atom,
wherein at least one Y atom is deuterium or at least one X atom is a carbon-13 atom.

4. The compound of claim 1, wherein at least one Y atom is deuterium atom.

5. The compound of claim 1, wherein at least three Y atoms are deuterium atoms.

6. The compound of claim 3, wherein at least one X atom is a carbon-13 atom.

7. The compound of claim 3, wherein at least two X atoms are carbon-13 atoms.

8. The compound of claim 1 of the formula V:

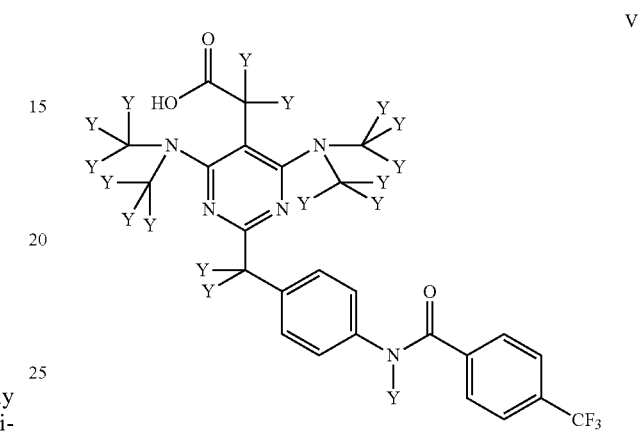

V wherein each Y atom is a hydrogen or a deuterium and at least one Y atom is a deuterium.

9. A compound of claim 1 of the formula

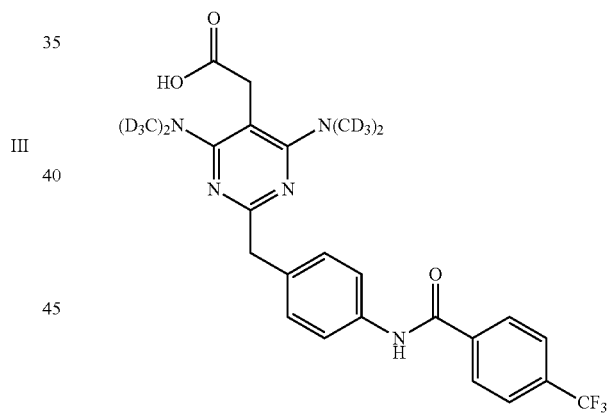

or a pharmaceutically acceptable salt thereof.

10. An amine salt compound comprising an acid compound according to claim 1 and a pharmaceutically acceptable amine.

11. The amine salt compound of claim 10, wherein the amine salt compound comprises a diamine salt comprising about two molar equivalents of the acid compound according to claim 1 and one molar equivalent of the diamine.

12. A pharmaceutical composition comprising the compound of claim 1 and a pharmaceutically acceptable excipient.

* * * * *